US011738197B2

(12) United States Patent
Verzal et al.

(10) Patent No.: US 11,738,197 B2
(45) Date of Patent: Aug. 29, 2023

(54) SYSTEMS AND METHODS FOR OPERATING AN IMPLANTABLE MEDICAL DEVICE BASED UPON SENSED POSTURE INFORMATION

(71) Applicant: INSPIRE MEDICAL SYSTEMS, INC., Golden Valley, MN (US)

(72) Inventors: Kevin Verzal, Lino Lakes, MN (US); John Rondoni, Plymouth, MN (US)

(73) Assignee: Inspire Medical Systems, Inc., Golden Valley, MN (US)

( * ) Notice: Subject to any disclaimer, the term of this patent is extended or adjusted under 35 U.S.C. 154(b) by 114 days.

(21) Appl. No.: 16/978,275

(22) PCT Filed: Jul. 24, 2020

(86) PCT No.: PCT/US2020/043442
§ 371 (c)(1),
(2) Date: Sep. 4, 2020

(87) PCT Pub. No.: WO2021/016536
PCT Pub. Date: Jan. 28, 2021

(65) Prior Publication Data

US 2021/0268279 A1 Sep. 2, 2021

Related U.S. Application Data

(60) Provisional application No. 62/878,531, filed on Jul. 25, 2019.

(51) Int. Cl.
*A61N 1/36* (2006.01)

(52) U.S. Cl.
CPC ........ *A61N 1/3611* (2013.01); *A61N 1/36139* (2013.01)

(58) Field of Classification Search
CPC .......................... A61N 1/3611; A61N 1/36139
USPC ........................................................... 607/42
See application file for complete search history.

(56) References Cited

U.S. PATENT DOCUMENTS 5,010,893 A 4/1991 Sholder
5,031,618 A 7/1991 Mullett
5,233,984 A 8/1993 Thompson
5,280,791 A 1/1994 Lavie
5,342,409 A 8/1994 Mullett
5,354,317 A 10/1994 Alt
5,472,453 A 12/1995 Alt
5,593,431 A 1/1997 Sheldon
(Continued)

FOREIGN PATENT DOCUMENTS

CN 105769122 B 10/2018
CN 109259733 A 1/2019
(Continued)

OTHER PUBLICATIONS

Girardin et al., "Sleep detection with an accelerometer actigraph: comparisons with polysomnography," Physiology & Behavior, vol. 72, Issue 1-2, Jan.-Feb. 2001, pp. 21-28.
(Continued)

*Primary Examiner* — Erin M Piateski
(74) *Attorney, Agent, or Firm* — Dicke, Billig & Czaja, PLLC

(57) ABSTRACT

A system and/or method to control operation of an implantable medical device in response to sensed posture information.

30 Claims, 9 Drawing Sheets

(56) References Cited

U.S. PATENT DOCUMENTS 5,722,996 A 3/1998 Bonnet et al.
5,732,696 A 3/1998 Rapoport et al.
5,902,250 A 5/1999 Verrier et al.
5,944,680 A 8/1999 Christopherson et al.
6,044,297 A 3/2000 Sheldon et al.
6,064,910 A 5/2000 Andersson et al.
6,161,041 A 12/2000 Stoop et al.
6,466,821 B1 10/2002 Pianca et al.
6,641,542 B2 11/2003 Cho et al.
6,658,292 B2 12/2003 Kroll et al.
6,731,984 B2 5/2004 Cho et al.
6,748,272 B2 6/2004 Carlson et al.
6,773,404 B2 8/2004 Poezevera et al.
6,964,641 B2 11/2005 Cho et al.
7,025,729 B2 4/2006 Chazal et al.
7,117,036 B2 10/2006 Florio
7,149,584 B1 12/2006 Koh et al.
7,155,278 B2 12/2006 King et al.
7,167,743 B2 1/2007 Heruth et al.
7,189,204 B2 3/2007 Ni et al.
7,252,640 B2 8/2007 Ni et al.
7,313,440 B2 12/2007 Miesel et al.
7,330,760 B2 2/2008 Heruth et al.
7,340,302 B1 3/2008 Falkenberg et al.
7,343,198 B2 3/2008 Behbehani et al.
7,366,572 B2 4/2008 Heruth et al.
7,371,220 B1 5/2008 Koh et al.
7,395,113 B2 7/2008 Heruth et al.
7,396,333 B2 7/2008 Stahmann et al.
7,447,545 B2 11/2008 Heruth et al.
7,473,227 B2 1/2009 Hsu et al.
7,491,181 B2 2/2009 Heruth et al.
7,510,531 B2 3/2009 Lee et al.
7,530,956 B2 5/2009 Lewicke et al.
7,542,803 B2 6/2009 Heruth et al.
7,572,225 B2 8/2009 Stahmann et al.
7,578,793 B2 8/2009 Todros et al.
7,590,455 B2 9/2009 Heruth et al.
7,660,632 B2 2/2010 Kirby et al.
7,664,546 B2 2/2010 Hartley et al.
7,678,058 B2 3/2010 Patangay et al.
7,680,537 B2 3/2010 Stahmann et al.
7,717,848 B2 5/2010 Heruth et al.
7,757,690 B2 7/2010 Stahmann et al.
7,766,842 B2 8/2010 Ni et al.
7,775,993 B2 8/2010 Heruth et al.
7,792,583 B2 9/2010 Miesel et al.
7,853,322 B2 12/2010 Bourget et al.
7,862,515 B2 1/2011 Chazal et al.
7,873,413 B2 1/2011 McCabe et al.
7,881,798 B2 2/2011 Miesel et al.
7,887,493 B2 2/2011 Stahmann et al.
7,896,813 B2 3/2011 Sowelam et al.
7,908,013 B2 3/2011 Miesel et al.
7,909,771 B2 3/2011 Meyer et al.
7,957,797 B2 6/2011 Bourget et al.
7,957,809 B2 6/2011 Bourget et al.
7,974,689 B2 7/2011 Volpe et al.
7,976,470 B2 7/2011 Patangay et al.
8,002,553 B2 8/2011 Hatlestad et al.
8,016,776 B2 9/2011 Bourget et al.
8,021,299 B2 9/2011 Miesel et al.
8,024,044 B2 9/2011 Kirby et al.
8,083,682 B2 12/2011 Dalal et al.
8,150,531 B2 4/2012 Skelton
8,175,720 B2 5/2012 Skelton et al.
8,192,376 B2 6/2012 Lovett et al.
8,209,028 B2 6/2012 Skelton et al.
8,231,555 B2 7/2012 Skelton et al.
8,231,556 B2 7/2012 Skelton et al.
8,265,759 B2 9/2012 Tehrani et al.
8,282,580 B2 10/2012 Skelton et al.
8,285,373 B2 10/2012 Ternes et al.
8,323,204 B2 12/2012 Stahmann et al.
8,323,218 B2 12/2012 Davis et al.
8,337,431 B2 12/2012 Heruth et al.
8,360,983 B2 1/2013 Patangay et al.
8,366,641 B2 2/2013 Wang et al.
8,475,388 B2 7/2013 Ni et al.
8,535,222 B2 9/2013 Ni et al.
8,548,770 B2 10/2013 Yuen et al.
8,626,281 B2 1/2014 Ternes et al.
8,679,030 B2 3/2014 Shinar et al.
8,688,190 B2 4/2014 Libbus et al.
8,696,589 B2 4/2014 Kwok et al.
8,718,783 B2 5/2014 Bolea et al.
8,738,126 B2 5/2014 Craig
8,758,242 B2 6/2014 Miesel et al.
8,801,624 B2 8/2014 Patangay et al.
8,803,682 B2 8/2014 Wong et al.
8,836,516 B2 9/2014 Wolfe et al.
8,838,245 B2 9/2014 Lin et al.
8,862,226 B2 10/2014 Ternes et al.
8,870,764 B2 10/2014 Rubin
8,892,205 B2 11/2014 Miller, III et al.
8,905,948 B2 12/2014 Davis et al.
8,909,329 B2 12/2014 Prakash et al.
8,915,741 B2 12/2014 Hatlestad et al.
8,934,970 B2 1/2015 Ternes et al.
8,938,299 B2 1/2015 Christopherson et al.
8,956,295 B2 2/2015 Ni et al.
8,961,413 B2 2/2015 Teller et al.
8,972,197 B2 3/2015 Jangle et al.
8,992,436 B2 3/2015 Pu et al.
9,026,223 B2 5/2015 Skelton et al.
9,031,650 B2 5/2015 McCabe et al.
9,056,195 B2 6/2015 Sabesan
9,060,880 B2 6/2015 Van Beest
9,159,223 B2 10/2015 Proud
9,204,798 B2 12/2015 Proud
9,218,574 B2 12/2015 Phillipps et al.
9,302,109 B2 4/2016 Sabesan
9,320,434 B2 4/2016 Proud
9,320,435 B2 4/2016 Proud
9,327,070 B2 5/2016 Skelton et al.
9,339,188 B2 5/2016 Proud
9,345,404 B2 5/2016 Proud
9,380,941 B2 7/2016 Proud
9,381,358 B2 7/2016 Ternes et al.
9,392,939 B2 7/2016 Proud
9,393,419 B2 7/2016 Libbus et al.
9,398,854 B2 7/2016 Proud
9,486,628 B2 11/2016 Christopherson et al.
9,498,627 B2 11/2016 Rosenberg et al.
9,526,422 B2 12/2016 Proud
9,538,954 B2 1/2017 Patangay et al.
9,545,227 B2 1/2017 Selvaraj et al.
9,566,436 B2 2/2017 Hoffer et al.
9,582,748 B2 2/2017 Proud et al.
9,586,048 B2 3/2017 Ternes et al.
9,610,030 B2 4/2017 Proud
9,623,248 B2 4/2017 Heruth et al.
9,655,559 B2 5/2017 Chan et al.
9,656,082 B2 5/2017 Denk
9,662,015 B2 5/2017 Proud et al.
9,662,045 B2 5/2017 Skelton et al.
9,675,268 B2 6/2017 Bauer et al.
9,675,281 B2 6/2017 Arnold et al.
9,681,838 B2 6/2017 Halperin et al.
9,687,177 B2 6/2017 Ramanan et al.
9,700,243 B2 7/2017 Nakayama et al.
9,704,209 B2 7/2017 Proud et al.
9,704,372 B2 7/2017 Oorschot et al.
9,706,957 B2 7/2017 Wu et al.
9,717,846 B2 8/2017 Skelton et al.
9,731,126 B2 8/2017 Ferree et al.
9,737,719 B2 8/2017 Skelton et al.
9,743,848 B2 8/2017 Breslow et al.
9,750,415 B2 9/2017 Breslow et al.
9,763,767 B2 9/2017 Abramson et al.
9,773,196 B2 9/2017 Sachs et al.
9,788,762 B2 10/2017 Auerbach
9,814,429 B2 11/2017 Lee et al.
9,821,165 B2 11/2017 Gross

(56) References Cited

U.S. PATENT DOCUMENTS 9,883,809 B2 2/2018 Klap et al.
9,889,299 B2 2/2018 Ni et al.
9,907,959 B2 3/2018 Skelton et al.
9,919,159 B2 3/2018 Skelton et al.
9,943,234 B2 4/2018 Dalal et al.
9,974,959 B2 5/2018 Moffitt et al.
9,987,488 B1 6/2018 Gelfrand et al.
9,993,179 B2 6/2018 Beest et al.
9,993,197 B2 6/2018 Proud
9,999,351 B2 6/2018 Proud
10,004,451 B1 6/2018 Proud
10,010,253 B2 7/2018 Eyal et al.
10,028,699 B2 7/2018 Libbus et al.
10,071,197 B2 9/2018 Skelton et al.
10,105,092 B2 10/2018 Franceschetti et al.
10,105,538 B2 10/2018 Bolea et al.
10,230,699 B2 3/2019 Juels
10,300,230 B2 5/2019 Flower et al.
10,328,267 B2 6/2019 Hatlestad et al.
10,632,306 B2 4/2020 Bolea et al.
RE48,024 E 6/2020 Bolea et al.
10,758,164 B2 9/2020 Derkx
10,898,709 B2 1/2021 Wagner et al.
11,123,023 B2 9/2021 Babaeizadeh
11,324,950 B2 5/2022 Dieken et al.
2003/0105497 A1 6/2003 Zhu et al.
2005/0061320 A1 3/2005 Lee et al.
2005/0080349 A1 4/2005 Okada et al.
2005/0085738 A1 4/2005 Stahmann et al.
2005/0148897 A1 7/2005 Cho et al.
2005/0197588 A1 9/2005 Freeberg
2005/0288728 A1 12/2005 Libbus et al.
2006/0247729 A1 11/2006 Tehrani et al.
2007/0032733 A1 2/2007 Burton
2007/0115277 A1 5/2007 Wang et al.
2007/0233194 A1 10/2007 Craig
2007/0240723 A1 10/2007 Hong et al.
2008/0021504 A1 1/2008 McCabe et al.
2008/0033304 A1 2/2008 Dalal et al.
2008/0051669 A1 2/2008 Meyer et al.
2008/0234556 A1 9/2008 Brooke et al.
2010/0010380 A1 1/2010 Panken et al.
2010/0030085 A1 2/2010 Ojeda et al.
2010/0174335 A1 7/2010 Stahmann et al.
2010/0286545 A1 11/2010 Wolfe et al.
2011/0015702 A1 1/2011 Ternes et al.
2011/0034811 A1 2/2011 Naujokat et al.
2011/0046499 A1 2/2011 Klewer et al.
2011/0060215 A1 3/2011 Tupin
2011/0066041 A1 3/2011 Pandia et al.
2011/0066064 A1 3/2011 Jangle et al.
2011/0172744 A1 7/2011 Davis et al.
2012/0179061 A1 7/2012 Ramanan et al.
2012/0184825 A1 7/2012 Ben David
2012/0192874 A1* 8/2012 Bolea .................. A61N 1/0556
128/202.16
2012/0265279 A1 10/2012 Zhu
2012/0290032 A1 11/2012 Cho et al.
2013/0172769 A1 4/2013 Arvind
2013/0165994 A1* 6/2013 Ternes ............... A61N 1/36114
607/59
2013/0245502 A1 9/2013 Lange et al.
2013/0253616 A1 9/2013 Libbus et al.
2014/0088373 A1 3/2014 Phillips et al.
2014/0358825 A1 12/2014 Phillipps et al.
2014/0364770 A1 12/2014 Slonneger et al.
2014/0371817 A1 12/2014 Mashiach et al.
2015/0094962 A1 4/2015 Hoegh et al.
2015/0164380 A1 6/2015 O'Dwyer et al.
2015/0164411 A1 6/2015 Selvaraj et al.
2015/0173672 A1 6/2015 Goldstein et al.
2015/0190089 A1 7/2015 Christopherson et al.
2015/0224307 A1 8/2015 Bolea et al.
2015/0238138 A1 8/2015 Lehmann et al.
2015/0238304 A1 8/2015 Lamraoui
2015/0238766 A1 8/2015 McCabe et al.
2015/0283381 A1 10/2015 Denk
2015/0283382 A1 10/2015 Denk et al.
2015/0374279 A1 12/2015 Takakura et al.
2016/0022204 A1 1/2016 Mostov
2016/0029949 A1 2/2016 Landesberg et al.
2016/0082262 A1* 3/2016 Parramon .......... A61N 1/36132
607/46
2016/0199215 A1 7/2016 Kopelman
2016/0213309 A1 7/2016 Sannholm et al.
2016/0256692 A1 9/2016 Baru
2016/0310046 A1 10/2016 Heinrich et al.
2016/0338648 A1 11/2016 Faisal et al.
2016/0354602 A1 12/2016 Keenan et al.
2016/0354603 A1 12/2016 Hansen et al.
2016/0354608 A1 12/2016 Keenan et al.
2016/0379041 A1 12/2016 Rhee et al.
2017/0042471 A1 2/2017 Meriheina
2017/0046563 A1 2/2017 Kim et al.
2017/0056669 A1 3/2017 Kane et al.
2017/0071533 A1 3/2017 Warren et al.
2017/0076474 A1 3/2017 Fu et al.
2017/0172459 A1 6/2017 Bernstein et al.
2017/0172494 A1 6/2017 Warren et al.
2017/0181691 A1 6/2017 Olivier
2017/0258374 A1* 9/2017 Ly ........................ A61B 5/7475
2017/0290528 A1 10/2017 Ternes et al.
2017/0312515 A1 11/2017 Ferree et al.
2017/0319109 A1 11/2017 Skelton et al.
2017/0347969 A1 12/2017 Thakur et al.
2017/0367646 A1 12/2017 Schmidt et al.
2018/0015282 A1 1/2018 Waner et al.
2018/0064372 A1 3/2018 Beest et al.
2018/0064388 A1 3/2018 Heneghan et al.
2018/0078174 A1 3/2018 Chan et al.
2018/0103895 A1 4/2018 Yao
2018/0153476 A1 6/2018 Annoni et al.
2018/0221660 A1 8/2018 Suri et al.
2018/0344208 A1 12/2018 Ogasawara et al.
2018/0368758 A1 12/2018 Winter et al.
2019/0008451 A1 1/2019 Horne
2019/0076098 A1 3/2019 Li et al.
2019/0099125 A1 4/2019 Schnall
2019/0133499 A1 5/2019 Auerbach
2019/0150772 A1 5/2019 Haraikawa et al.
2019/0150787 A1 5/2019 Murray et al.
2019/0175026 A1 6/2019 Verzal et al.
2019/0231257 A1 8/2019 Javed
2019/0279363 A1 9/2019 Steigauf et al.
2019/0314192 A1 10/2019 Raj et al.
2020/0054289 A1 2/2020 Shimol et al.
2020/0107775 A1 4/2020 de Chazal et al.
2020/0147376 A1 5/2020 Dieken et al.
2020/0163794 A1 5/2020 Goff et al.
2020/0254249 A1 8/2020 Rondoni et al.
2020/0297273 A1 9/2020 Gollakota et al.
2020/0391028 A1 12/2020 Verzal et al.
2021/0030295 A1 2/2021 Shute et al.
2021/0169378 A1 6/2021 Gerard et al.
2022/0000435 A1 1/2022 Babaeizadeh
2022/0095952 A1 3/2022 Schipper et al.
2022/0111201 A1 4/2022 Verzal et al.
2022/0134103 A1 5/2022 Elyahoodayan et al.
2022/0134104 A1 5/2022 Elyahoodayan et al.

FOREIGN PATENT DOCUMENTS

EP 1146433 A1 6/1985
EP 1711104 A1 10/2006
EP 2816968 B1 8/2018
KR 20190081320 A 7/2019
WO 2005018737 A1 3/2005
WO 2012154733 A1 11/2012
WO 2016016469 A1 2/2016
WO 2016195809 A1 12/2016
WO 2017098609 A1 6/2017
WO 2017183602 A1 10/2017
WO WO-2017184753 A1 * 10/2017 .......... A61N 1/3601
WO 2017211396 A1 12/2017

(56) References Cited

FOREIGN PATENT DOCUMENTS

| | | | |
|---|---|---|---|
| WO | 2018006121 | A1 | 1/2018 |
| WO | 2018016392 | A1 | 1/2018 |
| WO | 2020132315 | A1 | 6/2020 |
| WO | 2020169424 | A1 | 8/2020 |

OTHER PUBLICATIONS

PCT International Search Report and Written Opinion, Int'l Appl. No. PCT/US2020/043500, dated Oct. 26, 2020, pp. 1-14.

Invitation to Pay Additional Fees and, Where Applicable, Protest Fee (includes preliminary International Search Report), Int'l Appl. No. PCT/US2020/043442, dated Oct. 22, 2020, pp. 1-14.

"AASM clarifies hypopnea scoring criteria," American Academy of Sleep Medicine, Sep. 23, 2013, aasm.org/aasm-clarifies-hypopnea-scoring-criteria/.

Epstein et al., "Clinical Guideline for the Evaluation, Management and Long-term Care of Obstructive Sleep Apnea in Adults," Journal of Clinical Sleep Medicine, vol. 5, No. 3, 2009, pp. 263-276.

Immanuel et al., "Respiratory timing and variability during sleep in children with sleep-disordered breathing," J Appl Physiol 113, Sep. 27, 2012, pp. 1635-1642.

Morgenthaler et al., "Practice Parameters for the Medical Therapy of Obstructive Sleep Apnea," Sleep, vol. 29, No. 8, 2006, pp. 1031-1035.

Phurrough et al., "Decision Memo for Continuous Positive Airway Pressure (CPAP) Therapy for Obstructive Sleep Apnea (OSA) (CAG-00093R2)," U.S. Centers for Medicare & Medicaid Services, Mar. 13, 2008, www.cms.gov/medicare-coverage-database/details/nca-decision-memo.aspx?NCA.

Rodriguez, Julia, "What do AHI, RERA, Arousal and RDI mean?," The Sleep Blog, Advanced Sleep Medicine Services, Inc., www.sleepdr.com/the-sleep-blog/what-do-ahi-rera-arousal-and-rdi-mean/ ResMed 2019.

Redmond et al., "Cardiorespiratory-Based Sleep Staging in Subjects With Obstructive Sleep Apnea," IEEE Transactions on Biomedical Engineering, vol. 53, No. 3, Mar. 2006, pp. 1-12.

Stein et al., "Heart rate variability, sleep and sleep disorders," Sleep Medicine Reviews, vol. 16, Issue 1, Feb. 2012, pp. 47-66.

PCT International Search Report and Written Opinion, Int'l Appl. No. PCT /US82020/043405, dated Nov. 5, 2020, pp. 1-10.

PCT International Search Report and Written Opinion, Int'l Appl. No. PCT/US2020/043493, dated Oct. 22, 2020, pp. 1-13.

PCT International Search Report and Written Opinion, Int'l Appl No. PCT/US2020/043442, dated Dec. 14, 2020, pp. 1-15.

Schwartz et al., Therapeutic Electrical Stimulation of the Hypoglossal Nerve in Obstructive Sleep Apnea, Arch Otolaryngol Head Neck Surg, vol. 127, Oct. 2001, pp. 1216-1223.

* cited by examiner

SYSTEMS AND METHODS FOR OPERATING AN IMPLANTABLE MEDICAL DEVICE BASED UPON SENSED POSTURE INFORMATION

CROSS REFERENCE TO RELATED APPLICATION

This Utility Patent Application claims priority under 35 U.S.C. § 371 to International Application Serial No. PCT/US20/043442, filed Jul. 24, 2020, which claims the benefit of U.S. Provisional Patent Application Ser. No. 62/878,531, filed Jul. 25, 2019, all of which are incorporated herein by reference.

BACKGROUND

Many patients benefit from therapy provided by an implantable medical device. For example, a portion of the population suffers from various forms of sleep disorder breathing (SDB). In some patients, external breathing therapy devices and/or mere surgical interventions may fail to treat the sleep disordered breathing behavior. With these and other implantable medical device therapy applications, operation of such systems can be improved with reference to sensed patient information.

DETAILED DESCRIPTION

Figure 1:
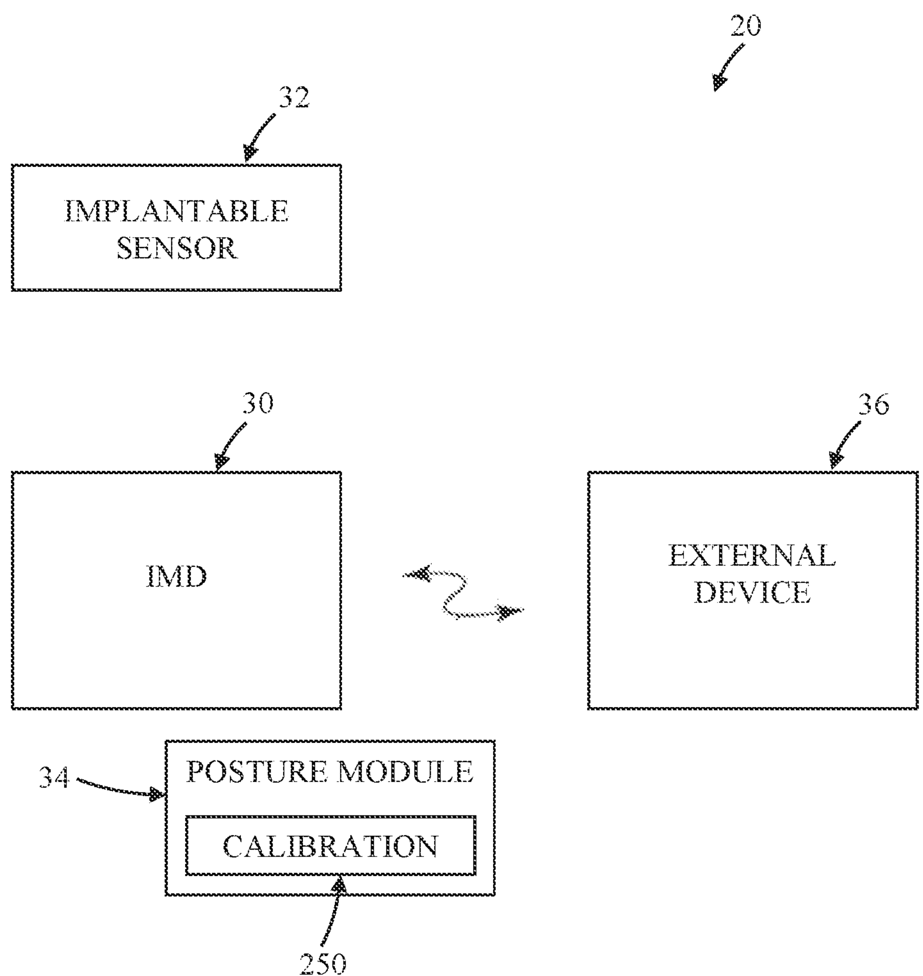
FIG. 1 is a block diagram schematically illustrating a patient care system in accordance with principles of the present disclosure.

In the following detailed description, reference is made to the accompanying drawings which form a part hereof, and in which is shown by way of illustration specific examples in which the disclosure may be practiced. It is to be understood that other examples may be utilized and structural or logical changes may be made without departing from the scope of the present disclosure. The following detailed description, therefore, is not to be taken in a limiting sense. It is to be understood that features of the various examples described herein may be combined, in part or whole, with each other, unless specifically noted otherwise.

At least some examples of the present disclosure are directed to systems and devices for diagnosis, therapy and/or other care of medical conditions. At least some examples may comprise implantable devices and/or methods comprising use of implantable devices.

At least some examples of present disclosure are directed to systems and methods for controlling at least one function or operation of an implantable medical device system, including an implantable medical device implanted within a patient, based upon sensed posture information of the patient. In some embodiments, one or more sensors implanted in the patient are utilized to sense or detect the posture information of the patient. In some embodiments, the operations of the implantable medical device system that are controlled in response to the sensed posture information relate to an operational mode of the implantable medical device in delivering therapy to the patient. In some embodiments, the systems and methods of the present disclosure incorporate one or more algorithms that result in an action being taken in response to a determination that the patient is in a designated posture or a determination that the probability the patient is in a designated posture is above a threshold; in other embodiments, the system and methods of the present disclosure incorporate one or more algorithms that result in an action being taken in response to a determination that the patient is not in a designated posture or a determination that the probability the patient is not in a designated posture is above a threshold. In some embodiments, the operations of the implantable medical device system that are controlled in response to the sensed posture information relate to determining or designating a current posture of the patient. In some embodiments, the operations of the implantable medical device system that are controlled in response to the sensed posture information relate to determining or designating that a current posture of the patient is not a designated or particular posture. In some embodiments, the operations of the implantable medical device system that are controlled in response to the sensed posture information relate to calibrating information signaled by one or more sensors. In some embodiments, the operations of the implantable medical device system that are controlled in response to the sensed posture information relate to generating information or data for review by the patient and/or caregiver.

In some examples, the systems and methods of the present disclosure are configured and used for sleep disordered breathing (SDB) therapy, such as obstructive sleep apnea (OSA) therapy, which may comprises monitoring, diagnosis, and/or stimulation therapy. However, in other examples, the system is used for other types of therapy, including, but not limited to, other types of neurostimulation or cardiac therapy. In some embodiments, such other implementations include therapies, such as but not limited to, central sleep apnea, complex sleep apnea, cardiac disorders, pain management, seizures, deep brain stimulation, and respiratory disorders.

One example of a patient therapy system 20 in accordance with principles of the present disclosure is schematically represented in FIG. 1. The patient therapy system 20 includes an implantable medical device (IMD) 30, one or more implantable sensors 32, a posture module or handler 34, and an optional external device 36. Details on the various components are provided below. In general terms, the IMD 30 is configured for implantation into a patient, and is configured to provide and/or assist in the performance of therapy to the patient. The implantable sensor 32 can assume various forms, and is generally configured for implantation into a patient and to at least sense a parameter indicative of a posture of the patient. The implantable sensor 32 can be carried by the IMD 30, can be connected to the IMD 30, or can be a standalone component not physically connected to the IMD 30. The posture module 34 receives information from the implantable sensor 32 and is programmed (or is connected to a separate module that is programmed) to recognize or identify or determine a current posture of the patient based, at least in part, upon information from the implantable sensor 32. In some embodiments, the posture module 34 is programmed (or is connected to a separate module that is programmed) to effect (or not effect) one or more control routines or the like relating to operation of the system 20. As described below, the posture module 34 can be incorporated by the IMD 30 (e.g., installed into a software application operated by the IMD 30), or can reside, either partially or entirely, with other components of the system 20. Where provided, the external device 36 can wirelessly communicate with the IMD 30, and is operable to facilitate performance of one or more operations as described below (e.g., the external device 36 can be used to initially program the IMD 30, and the IMD 30 then processes information (e.g., posture information) and delivers therapy independent of the external device 36). In other embodiments, the external device 36 can be omitted (e.g., the IMD 30, the implantable sensor 32 and the posture module 34 perform one or more of the operations described below without the need for an external device).

Figure 2:
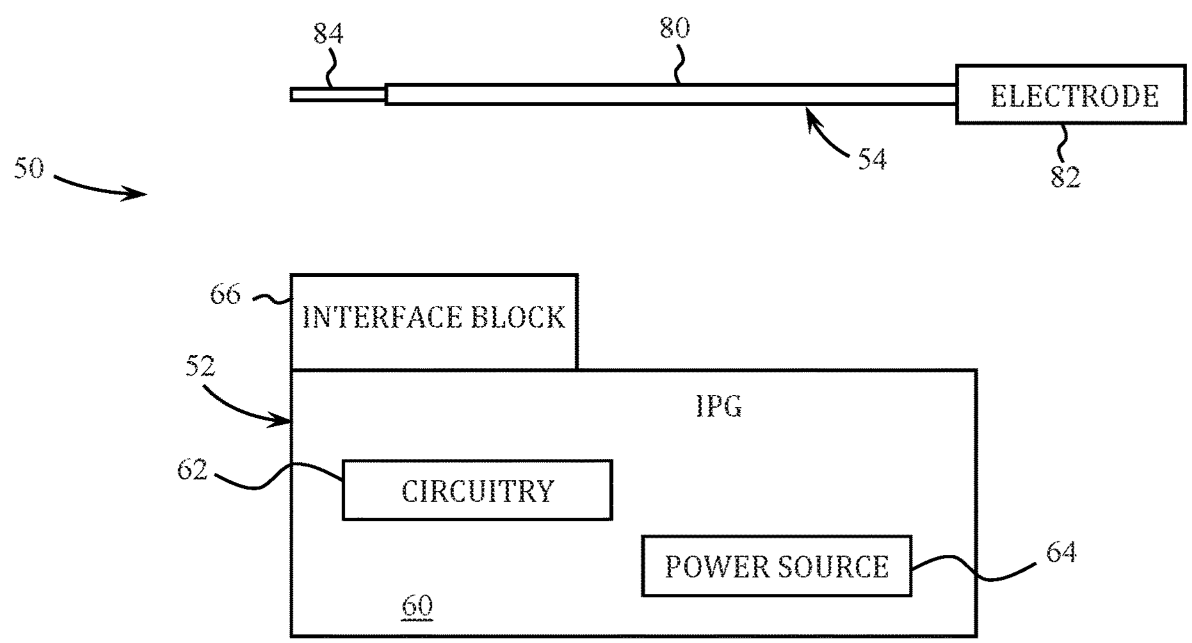
FIG. 2 is a block diagram schematically representing an implantable medical device useful with the care system of FIG. 1 and in a partially assembled state.

FIG. 2 is a block diagram schematically representing one example of an IMD 50 useful with the systems and methods of the present disclosure, for example as the IMD 30 of the system 20 of FIG. 1. The IMD 50 can include an implantable pulse generator (IPG) assembly 52 and a stimulation lead 54. The IPG assembly 52 can include a housing 60 containing circuitry 62 and a power source 64 (e.g., battery), and an interface block or header-connector 66 carried or formed by the housing 60. The housing 60 is configured to render the IPG assembly 52 appropriate for implantation into a human body, and can incorporate biocompatible materials and hermetic seal(s). The circuitry 62 can include circuitry components and wiring apparent to one of ordinary skill appropriate for generating desired stimulation signals (e.g., converting energy provided by the power source 64 into a desired stimulation signal), for example in the form of a stimulation engine. In some embodiments, the circuitry 62 can include telemetry components for communication with external devices as is known in the art. For example, the circuitry 62 can include a transmitter that transforms electrical power into a signal associated with transmitted data packets, a receiver that transforms a signal into electrical power, a combination transmitter/receiver (or transceiver), an antenna, etc.

In some embodiments, the stimulation lead 54 includes a lead body 80 with a distally located stimulation electrode 82. At an opposite end of the lead body 80, the stimulation lead 54 includes a proximally located plug-in connector 84 which is configured to be removably connectable to the interface block 66 (e.g., the interface block 66 can optionally include or provide a stimulation port sized and shaped to receive the plug-in connector 84 as is known in the art).

In general terms, the stimulation electrode 82 can optionally be a cuff electrode, and can include some non-conductive structures biased to (or otherwise configurable to) releasable secure the stimulation electrode 82 about a target nerve. Other formats are also acceptable. Moreover, the stimulation electrode 82 can include an array of electrode bodies to deliver a stimulation signal to a target nerve. In some non-limiting embodiments, the stimulation electrode 82 can comprise at least some of substantially the same features and attributes as described within at least U.S. Pat. No. 8,340,785 issued Dec. 25, 2012 and/or U.S. Patent Application Publication No. 2011/0147046 published Jun. 23, 2011 the entire teachings of each of which are incorporated herein by reference in their entireties.

In some examples, the lead body 80 is a generally flexible elongate member having sufficient resilience to enable advancing and maneuvering the lead body 80 subcutaneously to place the stimulation electrode 82 at a desired location adjacent a nerve, such as an airway-patency-related nerve (e.g. hypoglossal nerve, vagus nerve, etc.). In some examples, such as in the case of obstructive sleep apnea, the nerves may include (but are not limited to) the nerve and associated muscles responsible for causing movement of the tongue and related musculature to restore airway patency. In some examples, the nerves may include (but are not limited to) the hypoglossal nerve and the muscles may include (but are not limited to) the genioglossus muscle. In some examples, lead body 80 can have a length sufficient to extend from the IPG assembly 52 implanted in one body location (e.g. pectoral) and to the target stimulation location (e.g. head, neck). Upon generation via the circuitry 62, a stimulation signal is selectively transmitted to the interface block 68 for delivery via the stimulation lead 54 to such nerves.

Returning to FIG. 1, the implantable sensor 32 can assume various forms appropriate for implantation into a human patient, and generally includes a sensor component in the form of or akin to a motion-based transducer. In some embodiments, the motion-based transducer sensor component of the implantable sensor 32 can be or include an accelerometer (e.g., a single axis or multi-axis accelerometer), a gyroscope, a pressure sensor, etc., as is known in the art. The implantable sensor 32 can provide information along a single axis, or along multiples axes (e.g., three-axis accelerometer, three-axis gyroscope (three rotational axes), six-axis accelerometer (three linear axes and three rotational axes), nine-axis accelerometer (three linear axes, three rotational axes and three magnetic axes), etc. Regardless of an exact form, the sensor component of the implantable sensor 32 is capable of sensing, amongst other things, information indicative of a posture of the patient. As a point of reference, while information generated by the implantable sensor 32 is signaled to and acted upon by the posture module 34 as described below, information from the implantable sensor 32 can be utilized by other modules or engines (e.g., a therapy manager module that manages therapy delivered to the patient by the IMD 30 as described below).

The implantable sensor 32 can be connected to the IMD 30 in various fashions. For example, and with additional reference to the IMD 50 of FIG. 2, the implantable sensor 32 can include a lead body carrying the motion-based transducer sensor element at a distal end, and a plug-in connector at proximal end. The plug-in connector can be connected to the interface block 66 (e.g., the interface block 66 can include or provide a sense port sized and shaped to receive the plug-in connector of the implantable sensor 32), and the lead body extended from the IPG assembly 52 to locate the sensor element at a desired anatomical location. Accordingly, physical action-related information sensed via the motion-based transducer element is transmitted, via the interface block 66, to the circuitry 62.

Figure 3:
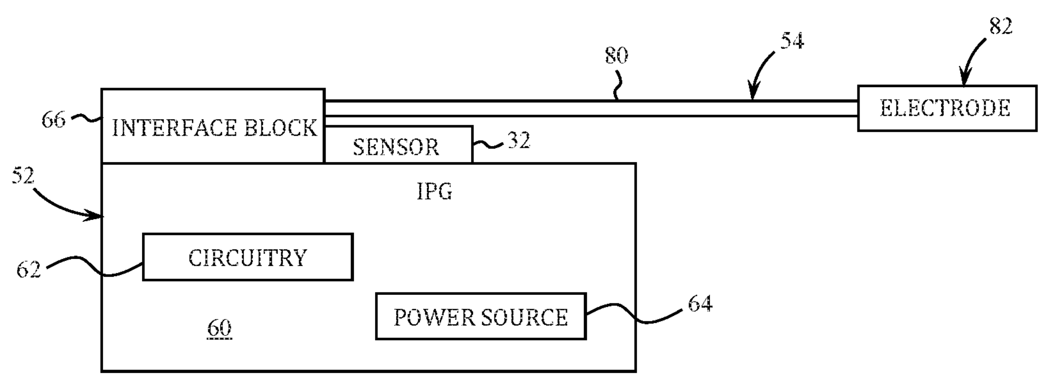
FIG. 3 is a block diagram schematically representing the implantable medical device of FIG. 2 in an assembled state and an implantable sensor in accordance with principles of the present disclosure assembled to the implantable medical device.

Alternatively, and as reflected by the block diagram of FIG. 3, the implantable sensor 32 can be physically coupled to the interface block 66, and thus carried by the IPG assembly 52 (e.g., the implantable sensor 32 can be considered a component of the IMD 50). Among other features, this optional arrangement may eliminate tunneling and/or other surgical steps ordinarily associated with placing sensing leads within a patient, as well as promote long term stability and ease securing the implantable sensor 32 because it occurs in conjunction with securing the IPG assembly 52. In some embodiments, the physical coupling of the implantable sensor 32 relative to the IPG assembly 52 is performed prior to implantation of those components.

In some embodiments, in order for the motion-based transducer-type implantable sensor 32 to fit on top of (e.g. next to) the housing 60 of the IPG assembly 52, a housing of the implantable sensor 32 has a size and shape that can maintain the motion-based transducer sensor component in a fixed orientation relative to the IPG assembly 52. This arrangement facilitates achieving and maintaining a proper orientation of the multiple orthogonal axes of the motion-based transducer sensor component relative to various axes of the patient's body, such as an anterior-posterior axis.

Figure 4:
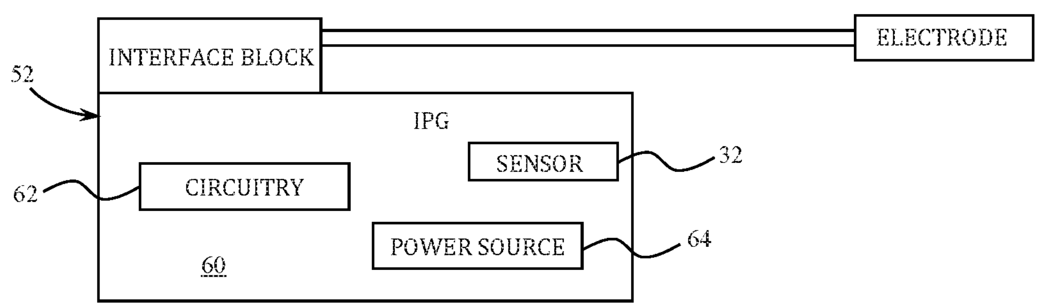
FIG. 4 is a block diagram of portions of another patient care system in accordance with principles of the present disclosure and including an implantable sensor carried within the housing of an implantable pulse generator assembly.

In related embodiments, and as reflected by the block diagram of FIG. 4, the implantable sensor 32 (and in particular the motion-based transducer sensor component as described above) can be incorporated into a structure of the interface block 66 or into a structure of the housing 60. With these and similar configurations, the sensor component of the implantable sensor 32 is electronically connected to the circuitry 62 within the housing 60 or other enclosure of the IPG assembly 52.

Figure 5:
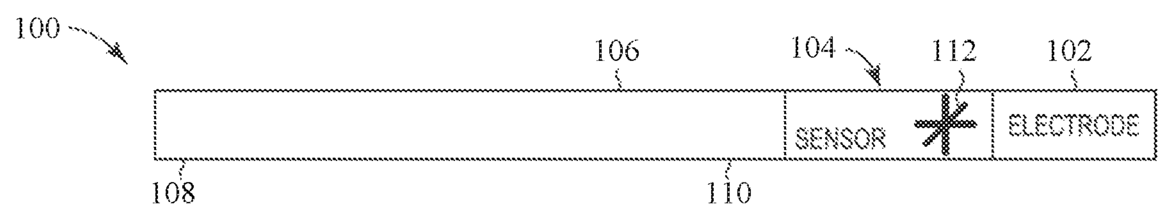
FIG. 5 is a block diagram schematically representing an example sensor lead useful with the patient care system of FIG. 1 and including a stimulation electrode and an implantable sensor.

In yet other embodiments, the implantable sensor 32 can be incorporated into a structure of the stimulation lead 54. For example, FIG. 5 is a block diagram schematically representing a stimulation lead 100 including a stimulation electrode 102 and a motion-based transducer sensor 104 (akin to the implantable sensor 32 described above), according to one example of the present disclosure. In some examples, the stimulation lead 100 comprises at least some of substantially the same features and attributes as the lead 54 in FIG. 2, except for additionally including the motion-based transducer sensor 104. As shown in FIG. 5, the lead 100 comprises a lead body 106 having a proximal end 108 configured to be removably connectable to a port of an IPG assembly (e.g., the interface block 68 of the IPG assembly 52 of FIG. 2) and an opposite distal end 110 at which the motion-based transducer sensor 104 and the electrode 102 are mounted. In some examples, the sensor 104 is located closer to the distal end 106 than the proximal end 104 of the lead 100 without necessarily being at the distal end 110 of the lead body 106. In some optional embodiments, a portion of the lead 100 at which the motion-based transducer sensor 104 is located includes a mechanism (e.g., a rotatable sleeve) to enable selective rotation of the motion-based transducer sensor 104, which in turns enables adopting a desired orientation of the different axes 112 of the motion-based transducer sensor 104 (for example where the motion-based transducer sensor 104 is a multi-axis accelerometer).

Figure 6:
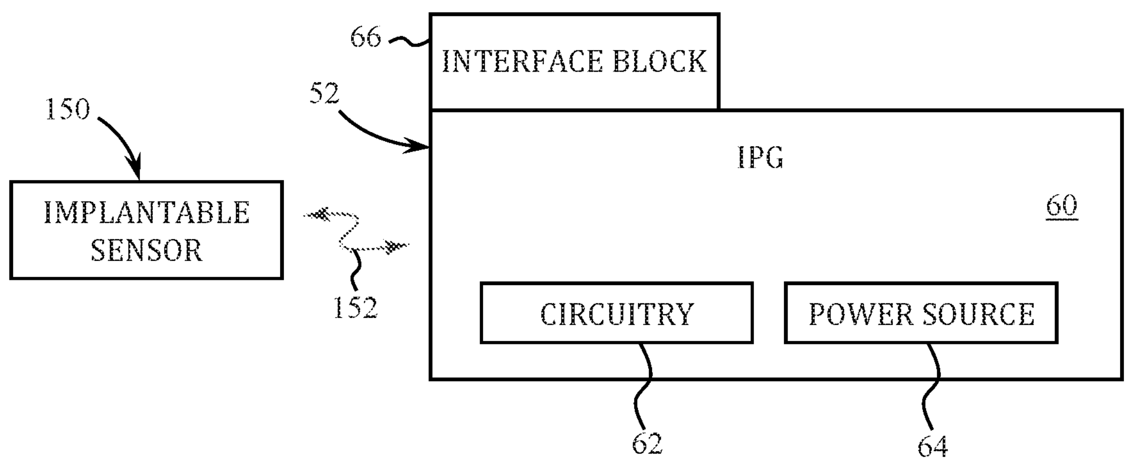
FIG. 6 is a block diagram schematically representing an example system including an implantable pulse generator assembly and a separate implantable sensor in accordance with principles of the present disclosure.

In yet other embodiments, the implantable sensor 32 can be wirelessly connected to the IMD 30. For example, FIG. 6 is a block diagram schematically representing a system including the IPG assembly 52 as described above and a separate implantable sensor 150, according to one example of the present disclosure. The implantable sensor 150 comprises at least some of substantially the same features and attributes as the previously described implantable sensors including the motion-based transducer sensor component, except for the lack of physical coupling of the implantable sensor 150 relative to IPG assembly 52; instead, the implantable sensor 150 is electrically and communicatively coupled wirelessly relative to the IPG assembly 52. With this in mind, the interface block 66 need not provide a sense port for the implantable senor 150 or the sense port can be used for a second sensor (not shown). In some embodiments, the circuitry 62 of IPG the assembly 52 and circuitry (not shown) of the implantable sensor 150 communicate via a wireless communication pathway 152 according to known wireless protocols, such as Bluetooth, NFC, MICS, 802.11, etc. with each of the circuitry 62 and the implantable sensor 150 including corresponding components for implementing the wireless communication pathway 152. In some examples, a similar wireless pathway is implemented to communicate with devices external to the patient's body for at least partially controlling the implantable sensor 150 and/or the IPG assembly 52, to communicate with other devices (e.g. other sensors) internally within the patient's body, or to communicate with other sensors external to the patient's body as described in greater detail below.

Figure 7A:
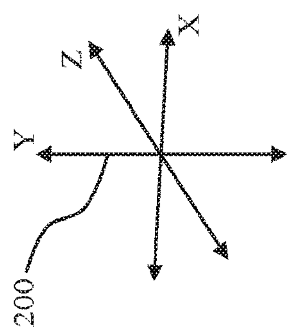
FIG. 7A schematically represents an axis orientation diagram of a three axis accelerometer useful as one non-limiting example of an implantable sensor of the present disclosure.

Regardless of how the implantable sensor 32 is associated with the IPG assembly 52, in some embodiments the implantable sensor 32 is configured to generate information indicative of sensed forces in three directions or axes. For example, in some embodiments, the implantable sensor 32 is a three-axis accelerometer that can sense or measure the static and/or dynamic forces of acceleration on three axes. Static forces include the constant force of gravity. By measuring the amount of static acceleration due to gravity, logic or programming (e.g., software) acting upon information from an accelerometer sensor can figure out the angle the sensor is tilted at with respect to the earth. By sensing the amount of dynamic acceleration, logic or programming acting upon information from the accelerometer sensor can find out fast and in what direction the sensor is moving. Single- and multi-axis models of accelerometers detect magnitude and direction of acceleration (or proper acceleration) as a vector quantity. With these and similar types of sensor constructions, an output from the implantable sensor can include vector quantities in one, two or three axes. For example, FIG. 7A provides an axis orientation indicator 200 of a three-axis accelerometer useful as the implantable sensor 32 in some non-limiting embodiments. The three axes and three outputs of the three-axis accelerometer are conventionally labeled as X, Y, and Z, with the three axes X, Y, Z being orthogonal to one other. With these and related constructions, efforts can be made to implant the implantable sensor 32 within the patient's body such that the axes X, Y, Z are in general alignment with planes or axes of the patient.

Figure 7B:
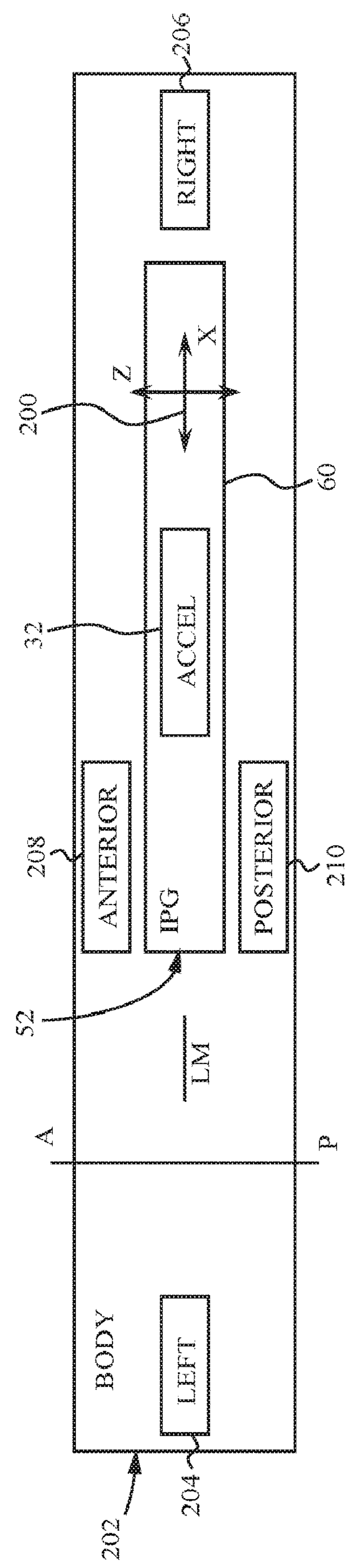
FIG. 7B is a block diagram schematically representing a sectional view of an example IPG assembly carrying an implantable sensor implanted within a body in association with an axis orientation diagram.

For example, in FIG. 7B, a patient's body 202 can be viewed as having a left side 204 and an opposite right side 206, along with an anterior portion 208 and an opposite posterior portion 210. A conventional coordinate system of the patient's body 202 includes an anterior-posterior (A-P) axis and a lateral-medial (L-M) axis as labeled in FIG. 7B, and a superior-inferior (S-I) axis (vertical or head-to-toe) that is into a plane of the view of FIG. 7B. With the non-limiting embodiment of FIG. 7B in which the implantable sensor 32 is a three-axis accelerometer disposed within the housing 60 of the IPG assembly 52, the implantable sensor 32 is arranged relative to the housing 60 and the housing 60 arranged relative to the patient's body 202 such that the sensor's X, Y, Z axes are approximately aligned with the patient's body coordinate system. For example, the Z axis of the implantable sensor can be aligned with A-P axis, the X axis aligned with the L-M axis, and the Y axis aligned with the S-I axis. A posture (including position) of the patient can be designated with reference to the body coordinate system, such that X, Y, Z information from the sensor 32 can be employed to determine posture when the sensor axes X, Y, Z are aligned with the body coordinate system axes. However, exact alignment can be difficult to achieve. Similar concerns may arise where the implantable sensor 32 is implanted at a location apart from the housing 60 of the IPG assembly 52. As described below, some methods of the present disclosure can include calibrating information signaled from the implantable sensor 32 for possible misalignment with the body coordinate system axes or other concerns relating to determining or designating a posture of the patient based on information from the implantable sensor 32. Calibration of the present disclosure can also address other possible concerns, such as the implantable sensor 32 (or the IPG assembly 52 with embodiments in which the implantable sensor 32 is carried in the housing 60) changing orientation relative to the patient's body following implant. For example, with certain patients and implant locations (e.g., high BMI patients, female patients, etc.), the pocket within which the device is implantable may shift between standing and laying down postures; calibration systems and methods of the present disclosure can account for these differences.

Returning to FIG. 1, regardless of a format of the implantable sensor 32, the posture module 34 is programmed to perform one or more operations as described below based upon information from the implantable sensor 32 (e.g., the implantable senor 32 output is an input to the posture module 34). In general terms, in some non-limiting examples the posture module 34 is programmed to detect, determine or designate, based at least in part upon information signaled by the implantable sensor 32, the current posture (including position) of the patient. In other non-limiting examples, the posture module 34 is programmed to detect, determine or designate, based at least in part upon information signaled by the implantable sensor 32, that the patient is not in a particular posture (e.g., the patient is not supine). As described below, some non-limiting embodiments of the present disclosure relate to methods for determining or designating the current posture, optionally including calibrating signaled information from the implantable sensor 32. The posture module 34 is further programmed (or signals information implicating the designated current posture to another module or engine that is programmed) to perform one or more operations or routines relating to control of the system 20 (e.g., controlling operations of the IMD 30, the implantable sensor 32, the external device 36, etc.) in some non-limiting embodiments. As described below, some non-limiting embodiments of the present disclosure relate to methods for acting upon the determined current posture. Other non-limiting examples of the present disclosure related to methods for acting upon a determination that the patient is not in a particular or designated posture. The posture module 34 can be further programmed (or signal information implicating the designated current posture to another module or engine that is programmed) to provide information to the patient and/or caregiver relating to the determined current posture (or other information of possible interest implicated by information from the implantable sensor 32). As described below, some non-limiting embodiments of the present disclosure relate to methods for generating and/or reporting information to the patient and/or caregiver. The posture module 34 (or the logic akin to the posture module 34 as described below) can be incorporated into a distinct module or engine programmed to perform certain tasks (e.g., logic of the posture module 34 as described below can be part of a therapy control engine and utilized in controlling stimulation therapy delivered to the patient). The posture module 34 (or the algorithms as described below) can reside partially or entirely with the IMD 30 (e.g., the circuitry 62 (FIG. 2)), partially or entirely with the external device 36, or partially or entirely with a separate device or component (e.g., the cloud, etc.).

Posture Determination

As implicated by the above, in some embodiments the posture module 34 is programmed or designed (e.g., appropriate algorithms) to detect, determine or designate a current posture of the patient based upon information from the implantable sensor 32. In at least this context, the term "posture" can refer at least to identifying whether a patient is in a generally vertical position or a lying down position, such as a supine position, a prone position, a left side position (e.g., left lateral decubitus), a right side position (e.g., right lateral decubitus), etc. In some instances, the term "posture" may sometimes be referred to as "body position".

In some examples, the posture module 34 rejects non-posture components from an accelerometer-type implantable sensor via low pass filtering relative to each axis of the multiple axes of the accelerometer sensor. In some examples, posture is at least partially determined via detecting a gravity vector from the filtered axes.

In some examples, one potential posture classification protocol implemented by the posture module 34 includes determining whether the patient is active or at rest. In some examples, when a vector magnitude of the acceleration measured via the accelerometer-type implantable sensor meets or exceeds a threshold (optionally for a period of time), the measurement may indicate the presence of non-gravitational components indicative of non-sleep activity. In some examples, the threshold is about 1.15 G. Conversely, measurements of acceleration of about 1 G (corresponding to the presence of the gravitational components only) may be indicative of rest.

In some examples, one potential posture classification protocol implemented by the posture module 34 includes determining whether at least an upper body portion (e.g., torso, head/neck) of the patient is in a generally vertical position (e.g., upright position) or lying down. In some examples, a generally vertical position may comprising standing or sitting. In some examples, this determination may observe the angle of the accelerometer-based implantable sensor between the Y axis and the gravitational vector, which sometimes may be referred to as a y-directional cosine. In some examples, when such an angle is less than 40 degrees, the measurement suggests the patient is in a generally vertical position, and therefore likely not asleep.

In some examples, if the measured angle (e.g., a y-directional cosine) is greater than 40 degrees, then the measured angle indicates that the patient is lying down. In this case, one example posture classification protocol implemented by the posture module 34 includes classifying sub-postures, such as whether the patient is in a supine position, a prone position, or in a lateral decubitus position. In some non-limiting examples, after confirming a likely position of lying down, the posture classification protocol determines if the patient is in a supine position or a prone position. In some examples, the determination of a supine state is made when an absolute value of the z-directional cosine (the angle of the accelerometer-type implantable sensor between the Z axis (calibrated to represent the A-P axis of the patient's body and the gravitational vector) is less than or equal to 45 degrees, and the determination of a prone state when the absolute value of the z-directional cosine is greater than or equal to 135 degrees. If neither of those criteria are satisfied, then the patient may be lying on their left or right side (e.g., lateral decubitus position). Accordingly, in some non-limiting examples, the posture classification protocol performs a further classification via the pitch angle such that the patient is designated as lying on their right side if the pitch angle is less than or equal to negative 45 degrees or greater than or equal to negative 135 degrees; the patient is designated as lying on their left side if the pitch angle is greater than or equal to 45 degrees or the pitch angle is less than or equal to 135 degrees. In some examples, a similar determination can be made using directional cosines.

The above explanations provide a few non-limiting examples of some posture determination or designation protocols implemented by the posture module 34. A number of other posture determination or designation techniques are also envisioned by the present disclosure, and can be function of the format of the implantable sensor 32 and/or other information provided by one or more additional sensors.

In some embodiments, the posture module 34 is programmed to distinguish between a supine sleep position and a generally supine reclined position. As a point of reference, a generally supine reclined position can be one in which the patient is on a recliner, on an adjustable-type bed, laying on a couch, or the like and not attempting to sleep (e.g., watching television) vs. sleeping in bed. An absolute vertical distance between the head and torso of the patient in the supine sleep position is less than the absolute vertical distance between the head and torso in the generally supine reclined position. Alternatively or in addition, in some embodiments, the posture module 34 is programmed to consider or characterize a position of the patient's neck and/or head and/or body position (e.g., as part of a determination of the patient's rotational position while lying down). For example, the posture module 34 can be programmed to estimate a position of the patient's neck based on body position. A determination that the patient's torso is slightly offset may imply different head positions. In some non-limiting embodiments, the systems and methods of the present disclosure can consider or characterize a position of the patient's neck and/or head via information from a sensor provided with a microstimulator that is implanted in the patient's neck or in conjunction with a sensor integrated into the stimulation lead. In other examples, two (or more) position-type sensors (e.g., accelerometers) can be provided, each implanted in a different region of the patient's body (e.g., torso, head, neck) and providing information to the posture module 34 sufficient to estimate neck and/or head and/or body positions of the patient.

Figure 8:
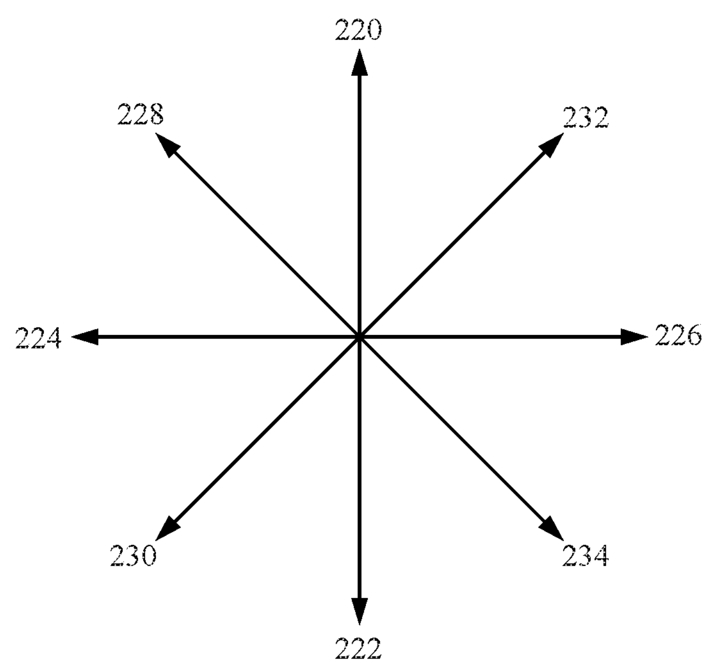
FIG. 8 schematically represents positional information obtained for a patient in a lying down position in accordance with some embodiments of the present disclosure.

In addition to, or as an alternative to, the above, in some embodiments, the systems and methods of the present disclosure can include the posture module 34 programmed to determine or designate lying down positions in addition to the four "primary" lying down positions described above (i.e., supine, prone, left lateral decubitus, and right lateral decubitus). For example, and with additional reference to FIG. 8, the lying down positions can be classified or characterized as including supine 220, prone 222, left lateral decubitus 224, right lateral decubitus 226, supine left 228, prone left 230, supine right 232, and prone right 234. The posture module 34 can be configured or programmed to identify the lying down positions of FIG. 8 in various manners, for example where the implantable sensor 32 is a three-axis accelerometer, the posture module 34 can be programmed to implement a 15 degree radial offset to information received from the implantable sensor 32 once a determination is made that the patient is lying down. A number of other techniques can be employed, and the number of lying down positions that can be classified by the posture module 34 is in no way limited to the information implicated by FIG. 8.

Additionally or alternatively, in some embodiments, the systems and methods of the present disclosure can include the posture module 34 programmed to determine or designate a current posture or position of the patient utilizing a temporal analysis or probabilistic based approached. For example, the posture module 34 can be programmed (e.g., a time averaging algorithm) to designate a current posture or position based upon a time average of information from the implantable sensor 32, thus minimizing the impact of small artifacts in the information from the implantable sensor 32 due to, for example, arm movement, leg movement, jerking, etc., especially when the patient is sleeping. By way of example, one approach for determining or designated that the patient is lying supine and sleeping can include reviewing a dot product of vector information from the implantable sensor 32 (e.g., vector information in a head-to-toe direction of the patient) with a gravity or vertical reference vector or head-to-toe (described in greater detail below); when the patient is lying supine and sleeping, this dot product will be approximately zero. If the patient randomly jerks an appendage while sleeping, the dot product of corresponding vector information from the implantable sensor 32 with the gravity or vertical reference vector may no longer be approximately zero yet the patient is still lying supine and asleep. By utilizing a time averaging or other probabilistic approach, the posture module 34 will not designate a "new" posture or position for the patient in response to the information generated by the implantable sensor 32 at the time the patient jerks his/her appendage. However, in some embodiments, the temporal analysis or probabilistic approach will be able to distinguish between the patient making a small movement while asleep and the patient rising from bed upon waking. In related embodiments, motion artifacts can be filtered by considering an overall magnitude of vector information from the implantable sensor 32 over short periods of time. For example, where the patient is lying down and asleep, the overall magnitude of vector information from the implantable sensor 32 will be approximately 1 g; if the patient jerks an appendage while sleeping, the overall magnitude will temporarily spike. Motion artifacts such as these can be filtered by ignoring temporary spikes in overall magnitude of less than a predetermined period of time (e.g., a few seconds). In other embodiments, a low pass filter can be applied to the implantable sensor signal to achieve similar results.

Additionally or alternatively, in some embodiments, the systems and methods of the present disclosure can include the posture module 34 programmed to determine or designate a current posture or position of the patient utilizing other probabilistic-based approaches. For example, the systems and methods can be programmed or operate an algorithm to perform an action when the probability that the patient is in a particular posture exceeds a certain threshold. Low or high thresholds may be appropriate depending upon the function that will be triggered by the detection. Likewise, the systems and method of the present disclosure optionally include taking an action when the probability that the patient is in a particular posture is below a particular threshold. In yet other examples, the systems and methods of the present disclosure include determining, based on information from the implantable sensor 32, that the patient is not in a particular posture (e.g., the system is programmed to take an action when information from the implantable sensor 32 is designated by the posture module 34 as implicating that the patient is not supine) or that the probability the patient is not in a particular posture is above a threshold. By way of non-limiting example, some of the probabilistic-based approaches or techniques of the present disclosure can include correlating the likelihood of the patient not being in a particular posture with the likelihood of the patient being in the particular posture. For example, where the "particular posture" is supine, a relationship of the probability of the patient not being supine ("not_probability_supine" can be correlated with the probability of the patient being supine ("probability_supine") as:

not_probability_supine=1−probability_supine

In practice, there may be different error sources in determining "not_probability_supine" and "probability_supine". For example, if different sensors or algorithms are used in the determination of each, the above equation would not hold and therefore, these two probabilities are distinct. This extends to the probability of multiple posture indications, each with a distinct error source. Also, the threshold (where applicable) that can be utilized for "not_probability_supine" may be different than the threshold utilized with for "1−probability_supine" if, for example, there is an interest to add a bias to the algorithm to reduce sensitivity to one error source at the expense of the other.

Additionally or alternatively, the systems and methods of the present disclosure can include calibrating to compensate, account, or address the possibility that a position of the implantable sensor 32 (from which posture determinations can be made) within the patient's body is unknown and/or has changed over time (e.g., migration, temporary re-orientation due to change in the implant pocket with changing posture as mentioned above). In some examples, the posture module 34 can be programmed (e.g., algorithm) to perform such calibration (indicated generally at 250 in FIG. 1), such as when the patient is determined to be walking because such a behavior is consistent with a gravity vector (e.g., of an accelerometer optionally used as the implantable sensor 32) pointing downward. In some examples, the posture module 34 can be programmed to perform a calibration, such as via measuring a gravity vector in at least two known patient orientations, of the implantable sensor/accelerometer 32 orientation. In some embodiments, where the output of the implantable sensor 32 is employed to detect postures of the patient in terms of the body coordinate system of the patient and the orientation of the implantable sensor 32 is such that the implantable sensor axes are not aligned with the body axes, a calibration can be applied to information provided by the implantable sensor 32 to a correct or account for this misalignment.

In some embodiments, calibration performed by the posture module 34 can include establishing or creating a vertical baseline gravity vector. For example, the vertical baseline gravity vector can be determined by the posture module 34 during times when the patient is deemed to be likely by upright (e.g., based on various information such as information from the implantable sensor, information from other sensors, time of day, patient history, etc., the likelihood or probability that the patient is upright and/or is engaged in an activity in which the patient is likely to be upright (e.g., walking) can be determined), and can be determined as a time average value during periods of higher activity. Once established, the vertical baseline gravity vector can be utilized by the posture module 34 to calibrate subsequently-received information from the implantable sensor 32. The vertical baseline gravity vector can be determined/re-set periodically (e.g., at pre-determined intervals).

In addition or alternatively, calibration performed by the posture module 34 can include establishing or creating a horizontal baseline gravity plane (alternatively a horizontal baseline vector or "head-to-toe" vector (relative to the patient's anatomy)). As a point of reference, the "vertical gravity vector" can be considered a vector truly aligned with the direction of gravity relative to earth. A "horizontal gravity plane" can be considered the plane that is truly orthogonal to the vertical gravity vector; a horizontal gravity vector (such as a head-to-toe vector) can be considered a vector that lies solely in the horizontal gravity plane. With this in mind, in some embodiments, the horizontal baseline gravity plane can be determined by the posture module 34 during times when the patient is deemed to be likely by lying down (e.g., based on various information such as information from the implantable sensor 32, information from other sensors, time of day, patient history, etc., the likelihood or probability that the patient is lying down and/or is engaged in a low activity in which the patient is likely to be lying down (e.g., sleeping) can be determined), and can be determined as a time average value during periods of low activity. Once established, the horizontal baseline gravity plane can be utilized by the posture module 34 to calibrate subsequently-received information from the implantable sensor 32. The horizontal baseline gravity plane can be determined/re-set periodically (e.g., at pre-determined intervals). In some embodiments, the horizontal baseline gravity plane can be determined by the cross product of various vectors obtained during periods of low activity so as to reduce or eliminate artifacts from rotation (e.g., the patient is lying down and changes positions from back, stomach, side, etc.). The cross product of two vectors obtained from the implantable sensor 32 when it is believed the patient is lying down should approximately equal the vertical baseline gravity vector; under circumstances where this is not true, it can be assumed that one or both of the vectors under consideration are not indicative of the patient in a lying down position and thus less useful in determining or designating a horizontal baseline gravity plane (or used as a horizontal baseline gravity vector).

In addition or alternatively, calibration performed by the posture module 34 can include establishing or creating a vertical baseline gravity vector and a horizontal baseline gravity plane (or horizontal baseline gravity vector otherwise within the horizontal baseline gravity plane) as described above (and useful for calibrating information from the implantable sensor 32 as part of a posture characterization or determination process), and confirming usefulness of the so obtained calibration values. For example, a dot product of a designated vertical baseline gravity vector and a designated vector of the horizontal baseline gravity plane is generated and compared to a threshold value. From this comparison, a usefulness of one or both of the designated vertical baseline gravity vector and the designated horizontal baseline gravity plane (or designated horizontal baseline gravity vector) is generated. For example, if the dot product is close to zero, then one or both of the designated vertical baseline gravity vector and the designated horizontal baseline gravity vector (or plane) are verified, and can be employed for calibrating information from the implantable sensor 32.

In addition or alternatively, calibration performed by the posture module 34 can include receiving a predetermined vertical baseline gravity vector and one or more predetermined horizontal baseline gravity vectors (e.g., indicative of prone, supine, left lateral decubitus, right lateral decubitus) useful for calibrating information from the implantable sensor 32. The predetermined baseline gravity vectors can be entered during the implant procedure (e.g., entered by a clinician using the external device 36 in the operating room), as part of a programming appointment (e.g., following implant, the patient mimics each posture or position of interest, and the posture module 34 is prompted (e.g., via the external device 36) to denote the corresponding vector information from the implantable sensor 32 as being the predetermined baseline gravity vector), as part of an in-home calibration procedure performed by the patient (e.g., the external device 36 is a smart phone or the like operating a software application), etc. In some embodiments, the posture module 34 is programmed to confirm the usefulness of the so-generated, predetermined baseline gravity vectors. For example, dot products and/or cross products of respective pairs of the predetermined baseline gravity vectors can be obtained to error check and ensure that all the predetermined baseline gravity vectors are approximately perpendicular (i.e., within 5 percent of a truly perpendicular relationship). To the extent any predetermined baseline gravity vector(s) are found to not be approximately perpendicular, the predetermined baseline gravity vector(s) can be further reviewed for possible usefulness as a calibration factor, or other steps taken to obtain viable predetermined baseline gravity vector(s). Conversely, to the extent the error check confirms viability of the predetermined baseline gravity vectors, the predetermined baseline gravity vectors can then be employed for calibrating information from the implantable sensor 32. In yet other embodiments, the posture module 34 can be programmed such that if the vectors are compared to reference vectors and there appears to be differences, a notification can be provided to the patient and/or clinician to re-preform the predetermined baseline gravity vector entry procedures.

In addition or alternatively, calibration performed by the posture module 34 can include determining an orientation of the implantable sensor 32 in the patient's body based upon respiratory and/or cardiac waveform polarity information provided by or derived from the implantable sensor 32 and/or other appropriate sensor components associated with the patient. In one aspect, motion signals have a significantly greater amplitude than respiration signals, and therefore the motion signals are extracted from a respiratory waveform or otherwise rejected. In some examples, this extraction may be implemented via an awareness of motion associated with an X axis or Y axis of an accelerometer sensor having signal power significantly greater than the signal power of a Z axis in the accelerometer sensor, such as where the accelerometer sensor is implanted in some examples such that its Z axis is generally parallel to an anterior-posterior axis of the patient's body. If a patient's respiration signal is largest in a particular axis (not necessarily aligned with one of X, Y, Z), motion artifact can be rejected by filtering signals not aligned with the axis where respiration is largest. In one aspect, motion signals sensed via the accelerometer sensor can be distinguished from the respiration signals sensed via the accelerometer according to the high frequency content above a configurable threshold. The respiratory and/or cardiac waveform polarity information can, for example, be reviewed to determine a likelihood of the patient being asleep (and thus lying down) and/or to determine a likelihood of the patient engaged in higher activity (and thus upright). Upon determining that the patient is currently likely lying down and/or likely upright, the posture module 34 can be programmed to review current information from the implantable sensor 32; to the extent the current information is not aligned with the determined likely position (e.g., it is determined that the patient is likely lying down and the current information from the implantable sensor 32 (e.g. vector information) does not directly implicate the patient is lying down), a calibration factor can be determined by the posture module 34 to be applied to information from the implantable sensor 32 based upon differences between the current information and expected.

In addition or alternatively, calibration performed by the posture module 34 can include determining an expected change in information from the implantable sensor 32 upon waking. Based upon information (current and/or tracked/historical) from the implantable sensor 32 and/or one or more additional sensors associated with the patient, it can be determined when the patient is likely asleep (and thus lying down) and when the patient is likely waking from sleep and changing to an upright posture (e.g., the patient gets out of bed in the morning following a night's sleep). Upon determining that the patient is currently likely changing posture upon waking from sleep, the posture module 34 can be programmed to review current information from the implantable sensor 32; to the extent the current information is not aligned with the determined likely position (e.g., it is determined that the patient is likely currently upright and the current information from the implantable sensor 32 (e.g., vector information) does not directly implicate the patient is upright), a calibration factor can be determined by the posture module 34 to be applied to information from the implantable sensor 32 based upon differences between the current information and expected.

In addition or alternatively, calibration performed by the posture module 34 can include reviewing current information from the implantable sensor 32 when the patient is likely asleep (and thus likely lying down). For example, the posture module 34 can incorporate, or received information from, an internal clock. With reference to information from the internal clock, the posture module 34 can be programmed to designate that the patient is likely lying down during certain hours of the day (e.g., 9:00 PM-7:00 AM, etc.). The "likely lying down" time frame can be preprogrammed to the posture module 34 and/or can be learned over time (based upon tracked/historical information). Upon determining that the patient is likely currently lying down, the posture module 34 can be programmed to review current information from the implantable sensor 32; to the extent the current information is not aligned with the determined likely position (e.g., it is determined that the patient is likely currently lying down and the current information from the implantable sensor 32 (e.g. vector information) does not directly implicate that the patient is lying down), a calibration factor can be determined by the posture module 34 to be applied to information from the implantable sensor 32 based upon differences between the current information and expected.

In addition or alternatively, calibration performed by the posture module 34 can include referencing information generated by a patient calibration program following implant. The patient calibration program can be implemented as part of a software application operated by the external device 36 (e.g., the external device 36 can be a smartphone or the like operating a software application programmed to effect patient calibration, a custom external programmer operating a patient calibration routine, a remote control, etc.), and walks the patient through a calibration sequence in which the patient is prompted to assume various postures or positions of interest; while the patient is in a particular posture or position, the posture module 34 is prompted to denote the current information from the implantable sensor 32 as corresponding to that particular posture or position. The results of this calibration sequence can be used to calibrate, adjust or correct information subsequently provided by the implantable sensor 32 and/or to "teach" the posture module 34 different orientations of the implantable sensor 32 relative to the patient. In some embodiments, the software application is programmed to prompt the patient to assume a vertical position and receive an indication that the patient is in the vertical position for establishing the predetermined vertical baseline gravity vector. Alternatively or in addition, the software application is programmed to prompt the patient to assume a horizontal supine position and receive an indication that the patient is in the horizontal supine position for establishing the predetermined horizontal supine baseline gravity vector. Other baseline vectors can be determined from the so-established predetermined horizontal supine baseline gravity vector (e.g., a predetermined horizontal prone baseline gravity vector, a predetermined horizontal left lateral decubitus baseline gravity vector, a predetermined horizontal right lateral decubitus baseline gravity vector, etc.). In yet other embodiments, the software application can be programmed to prompt the patent to assume one or more of a vertical position, a horizontal prone position, a horizontal left lateral decubitus position, and a horizontal right lateral decubitus position and receive a corresponding indication from the patient for establishing the predetermined vertical baseline gravity vector, the predetermined horizontal prone baseline gravity vector, the predetermined horizontal left lateral decubitus baseline gravity vector, and the predetermined horizontal right lateral decubitus baseline gravity vector.

In addition or alternatively, calibration performed by the posture module 34 can include a clinician programing at least one patient position to the posture module 34 while the patient is in the operating room (e.g., during the implantation procedure). For example, the clinician can program the posture module 34 that the patient is currently lying down position. Upon being information that the patient is currently lying down (or some other posture or position), the posture module 34 can be programmed to review current information from the implantable sensor 32; to the extent the current information is not aligned with a lying down positon (e.g., the current information from the implantable sensor 32 (e.g., vector information) does not directly implicate that the patient is lying down), a calibration factor can be determined by the posture module 34 to be applied to information from the implantable sensor 32 based upon differences between the current information and expected.

Operational Control

As alluded to above, in some non-limiting embodiments, the posture module 34 is programmed to control one or more operational features of the system 20 based upon a determined or designated posture (or communicates with another module or engine programmed to control an operational feature based upon posture as determined or designated by the posture module 34).

For example, the posture module 34 can be programmed (or communicates with another module or engine that is programmed) to select or implement a particular operational mode of the IMD 30 based upon the determined current posture. The "operational mode" of the IMD 30 can include one or more of stimulation parameters, sensing parameters, timing parameters, and diagnostic parameters. For example, the posture module 34 (or another module or engine provided with the system 20 and receiving posture information from the posture module 34) can be programmed with various, pre-determined stimulation therapy settings or modes appropriate for different sleeping positions of the patient (e.g., stimulation therapy settings or mode for one sleeping position (supine, prone, left lateral decubitus, right lateral decubitus, etc.) can differ from that of another sleeping position). When the posture module 34 determines that the patient is in a particular position, the IMD 30 is operated to implement the corresponding stimulation therapy settings or mode. With these and related embodiments, the posture module 34 (or another module or engine provided with the system 20 and receiving posture information from the posture module 34) can be programmed to automatically toggle operation of the IMD 30 between stimulation therapy settings in response to determined changes in the patient's posture. In yet other optional embodiments, the posture module 34 is programmed to determine a dot product value from vector information provided by the implantable sensor 32 as a threshold parameter for initiating (or suspending) delivery of therapy from the IMD 30. In yet other optional embodiments, when the posture module 34 determines that the patient is not in a particular posture or position, the IMD 30 is operated to implement a designated mode or stimulation therapy settings. With these and related embodiments, the posture module 34 (or another module or engine provided with the system 20 and receiving posture information from the posture module 34) can be programmed to automatically toggle operation of the IMD 30 between stimulation therapy settings in response to determination that the patient is not in a particular posture. In yet other optional embodiments, the systems and methods of the present disclosure include monitoring for the patient assuming various postures in a particular order, and then triggering a designated function when the ordering of postures is found to have occurred. With any of the examples of operational control described in the present disclosure, the particular control feature can be implemented upon determining or estimating that the patient is in a particular posture, or upon determining or estimating that the patient is not in a particular posture.

Additionally or alternatively, in some embodiments the posture module 34 can be programmed (or communicates with another module or engine of the system 20 that is programmed) to effect changes to a particular therapy being delivered to the patient by the IMD 30 based upon the determined posture and optionally other factors, akin to auto-titration. With these and related embodiments, the posture module 34 (or another module or engine of the system 20 communicating with the posture module 34) can, for example, automatically increase or decrease one or more parameters of a particular stimulation therapy mode, for example upon identifying that the patient is entering a different stage of sleep. In some examples, the posture module 34 (or another module or engine of the system 20 communicating with the posture module 34) incorporates algorithm(s) or programming to effect posture-based, automatic amplitude adjustments, providing a relatively consistent correlation between therapeutic amplitude and determined posture.

As a point of reference, stages of sleep are typically divided into non-rapid eye movement (non-REM) and rapid eye movement (REM). Non-REM sleep has three stages: N1, N2, and N3. N1 occurs right after falling asleep, and is typically characterized as "light sleep". During sleep, a person usually progresses through the three stages of non-REM sleep before entering REM sleep or stage. Obstructive sleep apnea may be less prevalent in N1 than REM.

Additionally or alternatively, in some embodiments the posture module 34 can be programmed (or communicates with another module or engine of the system 20 that is programmed) to effect changes to a particular therapy being delivered to the patient by the IMD 30 under circumstances where the patient is likely in a light state of sleep (e.g., N1), as derived from information of the implantable sensor 32. For example, the posture module 34 can be programmed to identify when the patient is likely asleep or attempting to sleep, and track changes in the patient's posture or position during the time the patient is deemed to be sleeping or attempting to sleep. Under circumstances where the system 20 is programmed to deliver therapy to the patient when the patient is sleeping, the posture module 34 (or another module or engine of the system 20 communicating with the posture module 34) can further be programmed to alter the currently-delivered therapy when the patient is determined to be changing positions while likely sleeping. For example, where it is determined that the patient has changed positions, or changed positions two or more times over a pre-determined time period (e.g., 5 minutes, 15 minutes, 30 minutes, etc.), it is likely that the patient is in a light state of sleep and that if stimulation therapy were continued to be delivered at pre-determined levels, this stimulation may make it more difficult for the patient to enter a deeper state of sleep. With these and other examples, the posture module 34 (or another module or engine of the system 20 communicating with the posture module 34) can be programmed to prompt the IMD 30 to pause the stimulation therapy being delivered to the patient and/or ramp down an intensity of the stimulation therapy being delivered to the patient. A "pause" can be considered a rapid ramping down to no stimulation therapy being delivered in some embodiments. The pause or ramping down can be effected for a pre-determined period of time or some other parameter (e.g., respiratory cycles, determination of unchanged sleep posture), and the IMD 30 prompted to re-commence or ramp up the stimulation therapy delivered to the patient.

Additionally or alternatively, in some embodiments the posture module 34 can be programmed (or communicates with another module or engine of the system 20 that is programmed) to effect changes to a particular therapy being delivered to the patient by the IMD 30 under circumstances where the patient is likely temporarily exiting a state of sleep, as derived from information of the implantable sensor 32. For example, the posture module 34 can be programmed to identify when the patient is likely asleep or attempting to sleep, and track changes in the patient's posture or position during the time the patient is deemed to be sleeping or attempting to sleep. Under circumstances where the system 20 is programmed to deliver therapy to the patient when the patient is sleeping, the posture module 34 (or another module or engine of the system 20 communicating with the posture module 34) can further be programmed to alter the currently-delivered therapy when the patient is determined to be likely temporarily exiting a state of sleep. For example, during the time period when the patient is normally sleeping, the patient may wake up and move to go to the bathroom, get a drink of water, etc. If stimulation therapy were continued to be delivered at pre-determined levels during the temporary exit from sleep, this stimulation may be undesirable for the patient. Thus, in some embodiments, where it is determined that the patient has a substantive change in posture during the time period when the patient is expected to be asleep, the posture module 34 (or another module or engine of the system 20 communicating with the posture module 34) can be programmed to prompt the IMD 30 to pause the stimulation therapy being delivered to the patient and/or ramp down an intensity of the stimulation therapy being delivered to the patient. In related embodiments, the pause or ramping down can be effected for a pre-determined period of time, and the IMD 30 prompted to re-commence or ramp up the stimulation therapy delivered to the patient; alternatively or in addition, the delivery of stimulation therapy can be re-commenced or ramped up upon determining that the patient has returned to a lying down position, automatically following expiration of a predetermined time period, following expiration of a predetermined time period and a determination that the patient is not moving about (e.g., an "auto-extended" pause), etc.

With optional embodiments described above in which the posture module 34 operates to effect an automatic pause or ramp down in delivered therapy for a predetermined time period, the posture module 34 can further be programmed (or communicates with another module or engine of the system 20 that is programmed) to incorporate or implement a pause or ramp down extension at the end of the predetermined time period under circumstances where it is determined that the patient is not in a sleep posture, is moving about, etc. In other optional embodiments, the posture module 34 (or another module or engine of the system 20 communicating with the posture module 34) is programmed to provide an auto-pause feature coupled to an automatic start time feature. For example, the system 20 can be programmed to initiate delivery of therapy at a predetermined time of day (e.g., 10:30 PM), but at the predetermined time of day after which stimulation therapy is to be delivered, this automatic start time is automatically paused until it is estimated or determined (e.g., information from the implantable sensor 32 via the posture module 34) that the patient is, or is likely, asleep.

Additionally or alternatively, in some embodiments the posture module 34 can be programmed (or communicates with another module or engine of the system 20 that is programmed) to perform an alert-type operation or routine under circumstances where the patient is likely in a position of poor sleep quality (and thus more likely to experience sleep disordered breathing), as derived from information of the implantable sensor 32. For example, the posture module 34 can be programmed to identify when the patient is likely asleep or attempting to sleep, and when the patient is determined to be in a particular posture or position (e.g., supine) based upon information from the implantable sensor 32, the posture module 34 (or another module or engine provided with the system 20 and communicating with the posture module 34) is programmed to prompt delivery of an inconvenient output to the patient intended to cause or encourage the patient to re-orient. For example, the IMD 30 can be prompted to increase the level of a currently-delivered stimulation therapy, prompted to deliver rapid multi-pulse stimulation, etc. Alternatively or in addition, the IPG assembly 52 can be prompted to vibrate. Alternatively or in addition, an audio alert can be generated at one or both of the IPG assembly 52 and the external device 36.

Additionally or alternatively, in some embodiments the posture module 34 can be programmed (or communicates with another module or engine of the system 20 that is programmed) to one or more of initiate, resume or ramp up (e.g., increase intensity) of delivered stimulation therapy upon determining that the patient has entered, or is likely to have entered, a state of sleep. For example, the posture module 34 can estimate or determine a plurality of current postures of the patient over time. Based upon stored algorithms or other predetermined parameters, when the plurality of postures implicates that the patient has entered a state of sleep, the posture module 34 prompts the IPG assembly 52 to begin delivering stimulation therapy. In related embodiments in which the posture module 34 is programmed to affect an "auto-pause" in delivered stimulation therapy (e.g., in response to a determination that the patient is awake or in a state of light sleep), the posture module 34 is programmed to prompt resuming of the stimulation therapy upon determining that the patient has, or has likely, entered a state of sleep based, at least in part, upon the posture information. In other related embodiments in which the system 20 is programmed to ramp down currently-delivered stimulation therapy under one or more circumstances (e.g., in response a determination that the patient is awake or in a state of light sleep), the posture module 34 is programmed to prompt ramping up of the stimulation therapy upon determining that the patient has, or has likely, entered a state of deep or deeper sleep based, at least in part, upon the posture information.

Additionally or alternatively, in some embodiments the posture module 34 can be programmed (or communicates with another module or engine of the system 20 that is programmed) to effect changes to therapy protocols or modes or other therapy parameters based upon learned or detected tendencies (e.g., sleep tendencies) of the patient over time as derived, at least in part, from information of the implantable sensor 32. For example, the posture module 34 (or another module or engine of the system 20 communicating with the posture module 34) can be programmed to track or record posture (or other information) during times when the patient is deemed to likely be asleep; the tracked information can include, for example, time of day, day of week, and the like. From this information, the posture module 34 can determine, over time (e.g., one or more days, weeks, or months), the patient's sleeping tendencies, for example the time periods the patient typically sleeps. The learned sleep tendencies determined by the posture module 34 can further be segmented by day of the week or consecutive days of the week (e.g., sleep tendencies on weekends and sleep tendencies on weekdays). The posture module 34 (or another module or engine of the system 20) can further be programmed to review a current time of day, a current day of week, or other sleep tendency parameter along with a current designated posture of the patient with the learned sleep tendency information to prompt operation of the IMD 30 (e.g., to initiate or end the delivery of therapy, such as stimulation therapy). For example, a current time of day and determined current posture can be recorded as a data pair, and compared with previously recorded sleep tendency information to determine whether the current time of day and current posture implicates that the patient is likely entering a state of sleep or exiting a state of sleep. Based upon this comparison, the IMD 30 can be prompted to initiate delivery of therapy (where the patient is likely entering a state of sleep) or end delivery of therapy (where the patient is likely exiting a state of sleep). Alternatively or in addition, the current day of week, current time of day, and current posture can be recorded as a data set, and compared with previously recorded sleep tendency information to determine whether the current time of day, current day of week and current posture implicates that the patient is likely entering a state of sleep or exiting a state of sleep. Based upon this comparison, the IMD 30 can be prompted to initiate delivery of therapy (where the patient is likely entering a state of sleep) or end delivery of therapy (where the patient is likely exiting a state of sleep).

Additionally or alternatively, in some embodiments the posture module 34 can be programmed (or communicates with another module or engine of the system 20 that is programmed) to determine contextual information of the patient during periods when the patient is awake as derived, at least in part, from information of the implantable sensor 32. For example, contextual information such as activity level, pelvic floor pressure, etc., can be determined or estimated based upon posture related information alone or in combination with additional, non-posture information.

Diagnostic Data

As alluded to above, in some non-limiting embodiments, the posture module 34 is programmed to provide information to the patient and/or caregiver relating to the determined current posture or other information of possible interest implicated by information from the implantable sensor 32, for example via the external device 36. As a point of reference, the IMD 30 can be configured to interface (e.g., via telemetry) with a variety of external devices. For example, the external device 36 can include, but is not limited to, a patient remote, a physician remote, a clinician portal, a handheld device, a mobile phone, a smart phone, a desktop computer, a laptop computer, a tablet personal computer, etc. The external device 36 can include a smartphone or other type of handheld (or wearable) device that is retained and operated by the patient to whom the IMD 30 is implanted. In another example, the external device 36 can include a personal computer or the like that is operated by a medical caregiver for the patient. The external device 36 can include a computing device designed to remain at the home of the patient or at the office of the caregiver.

With the above in mind, the posture module 34 can be programmed (or communicates with another module or engine of the system 20 that is programmed) to identify information from the implantable sensor 32 indicative of the occurrence of twiddler's syndrome. "Twiddler's syndrome" refers to the patient's deliberate or subconscious spinning or other manipulation of the IPG assembly 52 within the skin pocket, and can lead to malfunction of the IMD 30. For example, logic (e.g., algorithm) of the posture module 34 can recognize a substantive change in information from the implantable sensor 32 at, for example, a designated time of day. By way of non-limiting example, a time of day can be designated as the patient likely being in a lying down position or posture (e.g., 1:00 AM); where the information from the implantable sensor 32 is found to have a certain vector direction on a previous day at the designated time of day (or over several consecutive previous days at the designated time of day) and a substantively different vector direction on the current day at the designated time of day (e.g., an approximately opposite vector direction), it can be deemed there is a likelihood that the implantable sensor 32 has been flipped. Where the implantable sensor 32 is carried in the housing of the IPG assembly 52, this same information can be deemed as implicating a likelihood that the IPG assembly 52 has been flipped. Under these and similar circumstance, the posture module 34 can be programmed to notify or alert a clinician (via the external device 36) of the likely occurrence of twiddler's syndrome.

Alternatively or in addition, the posture module 34 can be programmed (or communicates with another module or engine of the system 20 that is programmed) to identify information from the implantable sensor 32 indicative of the occurrence of device migration. As a point of reference, in some embodiments the sensor component of the implantable sensor 32 is implanted in the patient apart from the IPG assembly 52, whereas in other embodiments the implantable sensor 32 is carried in the housing of the IPG assembly 52 that in turn is implanted in the patient. Regardless, common implantation techniques can include use of suture or similar attachment device that secures the device in question (e.g., the sensor component or the IPG assembly 52) to anatomy of the patient; over time, attachment between the device and the anatomy in question may lessen or deteriorate, with the device then migrating away from the exact implant location and/or orientation. With this in mind, logic (e.g., algorithm) of the posture module 34 can recognize changes in information from the implantable sensor 32 at, for example, a designated time of day, as implicating possible device migration. By way of non-limiting example, a time of day can be designated as the patient likely being in a lying down position or posture (e.g., 1:00 AM); where the information from the implantable sensor 32 is found to have a certain vector direction that is changing over time, it can be deemed there is a likelihood that the implantable sensor 32 has migrated from an initial implant location. Where the implantable sensor 32 is carried in the housing of the IPG assembly 52, this same information can be deemed as implicating a likelihood that the IPG assembly 52 has been migrated. Under these and similar circumstance, the posture module 34 can be programmed to notify or alert a clinician (via the external device 36) of the likely occurrence of device migration.

Alternatively or in addition, the posture module 34 can be programmed (or communicates with another module or engine of the system 20 that is programmed) to record posture-related information during certain activities of the patient and report the same to a clinician and/or the patient via the external device 36. For example, the posture module 34 can record or determine one or more of the percent of time the patient spends in each position during a sleeping event; the efficacy of therapy delivered by the IMD 30 in each position during a sleeping event; auto-titrated therapy setting (e.g., amplitude, electrode configuration, pulse characteristics, etc.) in each position during a sleeping event; etc. In related embodiments, the posture module 34 can operate (or communicate with) a sleep stage determination engine by which sleep stages can be determined. In some embodiments, such determination is made according to the relative stability of respiratory rate throughout the treatment period (e.g., during expected sleeping hours). In some non-limiting examples, the sleep determination engine determines and tracks the number of minutes awake, minutes in bed, posture, sleep/wake cycle, and/or number and depth of REM periods. In some examples, the posture module 34 can operate (or communicate with) a sleep quality engine to determine sleep quality according to, for example, a combination of a sleep time parameter, a sleep stage parameter, and a severity index parameter (e.g., apnea-hypopnea index measurement). The sleep stage can be determined via at least one of activity information, posture information, respiratory information, respiratory rate variability (RRV) information, heart rate variability (HRV) information, and heart rate information in some non-limiting embodiments. Other information that can be tracked by the posture module 34 (or other module or engine of the system 20) and delivered to a clinician and/or the patient via the external device 36 can include one or more of apnea-hypopnea index, respiratory rate, sleep disordered breathing, peripheral capillary oxygen saturation (SpO2), heart rate, snoring, etc. In yet other embodiments, the posture module 34 can be programmed to generate posture notifications at the external device 36 when stimulation (or other therapy) is being provided by the IMD 30.

Alternative Operational Modes

In some non-limiting examples of the present disclosure, the posture module 34 is programmed to detect a change in posture, and need not necessarily detect or designate a current posture of the patient (under some circumstances or under all circumstances). For example, the posture module 34 can be programmed or configured (e.g., operating logic or algorithm) such that when the patient is deemed or known to be asleep, the posture module 34 does not detect or designate a current posture of the patient (nor does any other module or engine of the system 20), but detects changes in posture, such as gross changes in posture (e.g., moving from left lateral decubitus to supine, supine to prone, etc.).

In other embodiments, the posture module 34 does not detect or determine posture (nor does any other module or engine of the system 20), but tracks the gravity vector of the implantable sensor 32 over time. With these and related embodiments, the posture module 34 is programmed or configured to allow a user (e.g., patient, caregiver, etc.) to define certain gravity vector orientations relative to the implantable sensor 32 (or relative to the IPG assembly 52 where the implantable sensor 32 is carried in the housing of the IPG assembly 52) that can be associated with different operations modes. Any number of these defined vector/modes could be established with variable ranges of affect. By way of non-limiting example, the posture module 34 (or other module or engine of the system 20) can be programmed or configured to activate therapy delivery during a defined time period when no or minimal motion by the patient is detected, and the monitored gravity vector (or other monitored patient information related to posture) is within a predetermined range.

In addition or alternatively, changes in the monitored gravity vector of a certain or pre-determined magnitude can be used to reset a therapy ramp (e.g., therapy is being delivered at a predetermined level or intensity, and a detected change in the monitored gravity vector is sufficient to prompt the ramping down of the delivered therapy level; delivery of the ramped down or lower level therapy continues until the monitored gravity vector returns to the predetermined range (e.g., implicating that the "change" in the patient's status is complete) and the delivered therapy is ramped up to the predetermined level or intensity). In other embodiments, when monitoring the gravity vector over time, the system can be programmed to make therapy changes based on at least one of the current vector, a change in the vector (e.g., vector, cosine math), or repeating change in the vector (e.g., implicating walking, breathing, etc.).

Figure 9A:
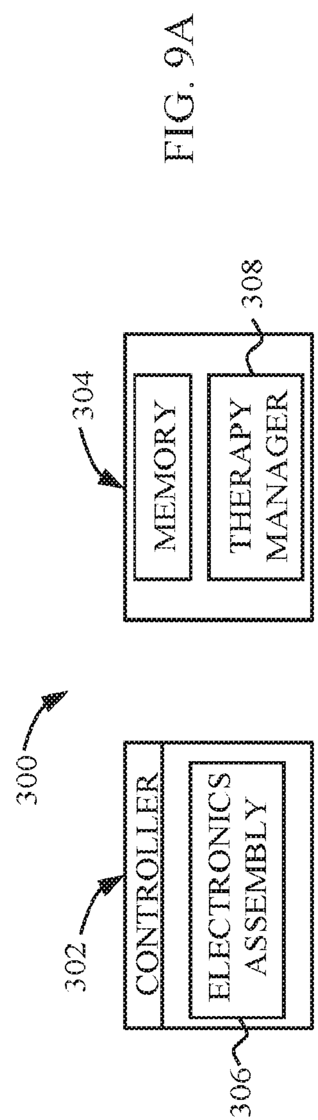
FIG. 9A is a block diagram schematically representing an example control portion.

As implicated by the above descriptions, one or both of the IMD 30 and the external device 36 includes a controller, control unit, or control portion that prompts performance of designated actions. FIG. 9A is a block diagram schematically representing a control portion 300, according to one example of the present disclosure. In some examples, the control portion 300 includes a controller 302 and a memory 304. In some examples, the control portion 300 provides one example implementations of a control portion forming a part of, implementing, and/or managing any one of devices, systems, assemblies, circuitry, managers, engines, functions, parameters, sensors, electrodes, modules, and/or methods, as represented throughout the present disclosure in association with FIGS. 1-8.

In general terms, the controller 302 of the control portion 300 comprises an electronics assembly 306 (e.g., at least one processor, microprocessor, integrated circuits and logic, etc.) and associated memories or storage devices. The controller 302 is electrically couplable to, and in communication with, the memory 304 to generate control signals to direct operation of at least some the devices, systems, assemblies, circuitry, managers, modules, engines, functions, parameters, sensors, electrodes, and/or methods, as represented throughout the present disclosure (e.g., the posture module 34 (FIG. 1) can be a software program stored on a storage device, loaded onto the memory 304, and executed by the electronics assembly 306). In addition, and in some examples, these generated control signals include, but are not limited to, employing therapy manager 308 stored in the memory 304 to at least manage therapy delivered to the patient, for example therapy for sleep disordered breathing, and/or manage and operate designated physical action sensing in the manner described in at least some examples of the present disclosure. It will be further understood that the control portion 300 (or another control portion) may also be employed to operate general functions of the various therapy devices/systems described throughout the present disclosure.

In response to or based upon commands received via a user interface (e.g. user interface 310 in FIG. 9C) and/or via machine readable instructions, the controller 302 generates control signals to implement therapy implementation, therapy monitoring, therapy management, and/or management and operation of designated physical action sensing and control in accordance with at least some of the previously described examples of the present disclosure. In some examples, the controller 302 is embodied in a general purpose computing device while in some examples, the controller 302 is incorporated into or associated with at least some of the associated devices, systems, assemblies, circuitry, sensors, electrodes, components of the devices and/or managers, engines, parameters, functions etc. described throughout the present disclosure.

For purposes of the present disclosure, in reference to the controller 302, with embodiments in which the electronics assembly 306 comprises or includes at least one processor, the term "processor" shall mean a presently developed or future developed processor (or processing resources) or microprocessor that executes sequences of machine readable instructions contained in a memory. In some examples, execution of the sequences of machine readable instructions, such as those provided via the memory 304 of the control portion 300 cause the processor to perform actions, such as operating the controller 302 to implement sleep disordered breathing (SDS) therapy and related management and/or management and operation of designated physical action sensing, as generally described in (or consistent with) at least some examples of the present disclosure. The machine readable instructions may be loaded in a random access memory (RAM) for execution by the processor from their stored location in a read only memory (ROM), a mass storage device, or some other persistent storage (e.g., non-transitory tangible medium or non-volatile tangible medium, as represented by the memory 304. In some examples, the memory 304 comprises a computer readable tangible medium providing non-volatile storage of the machine readable instructions executable by a process of the controller 302. In other examples, hard wired circuitry may be used in place of or in combination with machine readable instructions to implement the functions described. For example, the electronics assembly 306 may be embodied as part of at least one application-specific integrated circuit (ASIC), at least one integrated circuit, a microprocessor and ASIC, etc. In at least some examples, the controller 302 is not limited to any specific combination of hardware circuitry and machine readable instructions, nor limited to any particular source for the machine readable instructions executed by the controller 302.

Figure 9B:
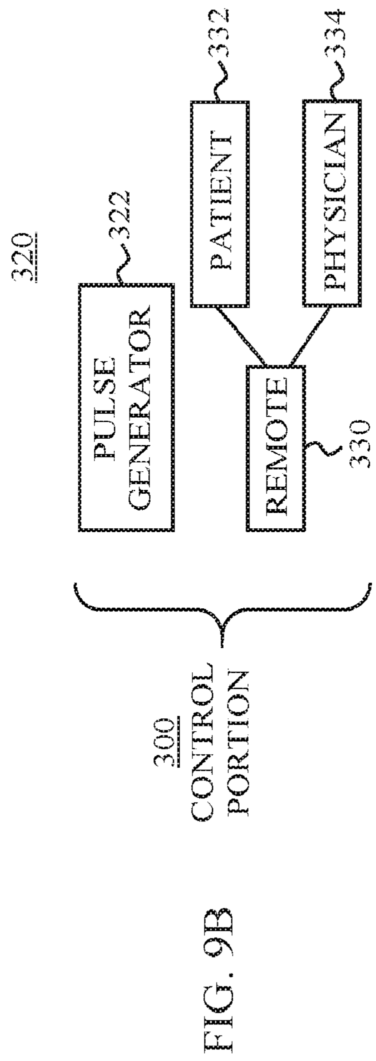
FIG. 9B is a diagram schematically representing at least some examples different modalities of the control portion of FIG. 9A.
Figure 9C:
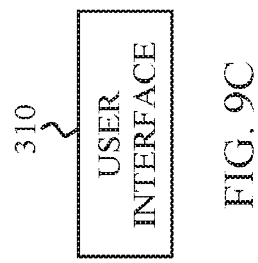
FIG. 9C is a block diagram schematically representing an example user interface.

FIG. 9B is a diagram 320 schematically illustrating at least some manners in which the control portion 300 can be implemented, according to one example of the present disclosure. In some examples, the control portion 300 is entirely implemented within or by an IPG assembly 322, which has at least some of substantially the same features and attributes as the IPG assembly 52 as previously described in association with at least FIG. 2. In some examples, the control portion 300 is entirely implemented within or by a remote control 330 (e.g. a programmer) external to the patient's body, such as a patient control 332 and/or a physician control 334. In some embodiments, the remote control 330 is akin to the external device 36 (FIG. 1) described above. In some examples, the control portion 300 is partially implemented in the IPG assembly 322 and partially implemented in the remote control 330 (at least one of the patient control 332 and the physician control 334). In some examples the control portion 300 may be implemented via a server accessible via the cloud and/or other network pathways. In some examples, the control portion 300 may be distributed or apportioned among multiple devices or resources such as among a server, an IMD, and/or a user interface In some examples, in association with the control portion 300, the user interface (310 in FIG. 9C) is implemented in the remote control 330. FIG. 9C is a block diagram schematically representing the user interface 310, according to one example of the present disclosure. In some examples, the user interface 310 forms part or and/or is accessible via a device external to the patient and by which the therapy system may be at least partially controlled and/or monitored. The external device hosting the user interface 310 may be a patient remote (e.g., 332 in FIG. 9B, for example a smartphone operating a custom software application), a physician remote (e.g., 334 in FIG. 9B) and/or a clinician portal. In some examples, the user interface 310 comprises a user interface or other display that provides for the simultaneous display, activation, and/or operation of at least some of the various systems, assemblies, circuitry, engines, sensors, components, modules, functions, parameters, as described in association with FIGS. 1-8. In some examples, at least some portions or aspects of the user interface 310 are provided via a graphical user interface (GUI), and may comprise a display and input.

Returning to FIG. 1, information from the implantable sensor 32, including the motion-based transducer sensor component, can optionally utilized to sense or detect other parameters associated with the patient, that may or may not include involuntary actions. Moreover, in some embodiments, the IMD 30 can be controlled to operate in response to involuntary actions by the patient as sensed by the implantable sensor 32. Non-limiting examples of some possible control features implemented by the systems and methods of the present disclosure can comprise at least some of substantially the same features and attributes as described within at least U.S. application Ser. No. 16/092,384, filed Oct. 9, 2018 and entitled "ACCELEROMETER-BASED SENSING FOR SLEEP DISORDERED BREATHING (SDB) CARE", the entire teachings of which are incorporated herein by reference. In related embodiments, the systems of the present disclosure can include one or more additional implantable sensors (in addition to the implantable sensor 32). Information signaled by the one or more additional implantable sensors can optionally be employed (along with information from the implantable sensor 32) as part of the recognition or identification of an occurrence of a posture of the patient as described above. Alternatively or in an addition, the information signaled by the one or more additional implantable sensors can be employed in monitoring the patient, formulating a therapy regimen, etc., as described, for example, in U.S. application Ser. No. 16/092,384.

Although specific examples have been illustrated and described herein, a variety of alternate and/or equivalent implementations may be substituted for the specific examples shown and described without departing from the scope of the present disclosure. This application is intended to cover any adaptations or variations of the specific examples discussed herein.

The invention claimed is:

1. A care system comprising:

a first implantable sensor to detect posture information of a patient;

an implantable medical device (IMD) for delivering stimulation therapy to the patient;

wherein the care system is programmed to affect operation of the IMD based upon the detected posture information; and a posture module programmed to calibrate information signaled by the first implantable sensor to address a possible change in position of the first implantable sensor relative to the patient over time.

2. The care system of claim 1, wherein the care system is configured to provide care for a patient with sleep disordered breathing (SDB), including delivering SDB stimulation therapy to the patient.

3. The care system of claim 1, wherein the posture module is programmed to determine that the patient is not in a designated posture based upon the detected posture information.

4. The care system of claim 1, wherein the care system is programmed to:

determine a current posture of the patient based upon the detected posture information;

store a plurality of determined current postures over time; and alter a currently-delivered stimulation therapy when the plurality of determined current postures indicates that the patient is in a state of light sleep.

5. The care system of claim 1, wherein the care system is programmed to:

determine a current posture of the patient based upon the detected posture information;

store a plurality of determined current postures over time; and initiate or resume delivery of stimulation therapy when the plurality of determined current postures indicates that the patient has entered a state of sleep.

6. The care system of claim 5, wherein the care system is programmed to ramp up an intensity of a currently-delivered stimulation therapy over a period of time upon determining that the patient has entered a state of sleep.

7. The care system of claim 1, wherein the care system is programmed such that when the patient is deemed to be asleep, a gross change in posture is determined from the detected posture information.

8. The care system of claim 1, wherein the posture module is programmed to determine a vertical baseline gravity vector for calibrating information signaled by the first implantable sensor.

9. The care system of claim 8, wherein the posture module is programmed to determine the vertical baseline gravity vector as a time average position during a plurality of time periods in which the patient is designated as being upright.

10. The care system of claim 1, wherein the posture module is programmed to determine a horizontal baseline gravity plane for calibrating information signaled by the first implantable sensor.

11. The care system of claim 10, wherein the first implantable sensor is configured to provide vector information in at least one of three orthogonal axes, and further wherein the posture module is programmed to calibrate the vector information in view of the horizontal baseline gravity plane.

12. The care system of claim 11, wherein the posture module is programmed to determine the horizontal baseline gravity plane based upon information signaled by the first implantable sensor during at least one time period in which the patient is designated as being at least one of inactive and sleeping.

13. The care system of claim 12, wherein the posture module is programmed to determine the horizontal baseline gravity plane as a time average position during a plurality of time periods in which the patient is designated as being inactive.

14. The care system of claim 12, wherein the horizontal baseline gravity plane implicates horizontal baseline gravity vectors extending in the horizontal baseline gravity plane, and further wherein the posture module is programmed to verify the determined horizontal baseline gravity plane by reviewing a cross product of horizontal vectors included in the information signaled by the first implantable sensor during the at least one time period in which the patient is designated as being inactive.

15. The care system of claim 14, wherein the posture module is programmed to validate the determined horizontal baseline gravity plane when the reviewed cross product approximately equals a determined vertical baseline gravity vector.

16. The care system of claim 15, wherein the posture module is programmed to determine a vertical baseline gravity vector and to verify the determined horizontal baseline gravity plane and the determined vertical baseline gravity vector by reviewing a dot product of the determined vertical baseline gravity vector and one or more horizontal baseline gravity vectors of the determined horizontal baseline gravity plane.

17. The care system of claim 16, wherein the posture module is programmed to validate the determined vertical baseline gravity vector and the determined horizontal baseline gravity plane when the reviewed dot product approximately equals zero.

18. The care system of claim 1, wherein the posture module is programmed to receive a predetermined vertical baseline gravity vector, a predetermined horizontal supine baseline gravity vector, a predetermined horizontal prone baseline gravity vector, a predetermined horizontal left lateral decubitus baseline gravity vector, and a predetermined horizontal right lateral decubitus baseline gravity vector for calibrating information signaled by the first implantable sensor.

19. The care system of claim 18, wherein the posture module is programmed to validate the predetermined vertical baseline gravity vector, the predetermined horizontal supine baseline gravity vector, the predetermined horizontal prone baseline gravity vector, the predetermined horizontal left lateral decubitus baseline gravity vector, and the predetermined horizontal right lateral decubitus baseline gravity vector by reviewing at least one of:

a dot product of the predetermined vertical baseline gravity vector with at least one of the predetermined horizontal supine baseline gravity vector, the predetermined horizontal prone baseline gravity vector, the predetermined horizontal left lateral decubitus baseline gravity vector, and the predetermined horizontal right lateral decubitus baseline gravity vector; and a cross product of a respective pair of the predetermined horizontal supine baseline gravity vector, the predetermined horizontal prone baseline gravity vector, the predetermined horizontal left lateral decubitus baseline gravity vector, and the predetermined horizontal right lateral decubitus baseline gravity vector.

20. The care system of claim 19, wherein the posture module is programmed to validate the predetermined vertical baseline gravity vector when the reviewed dot product approximately equals zero.

21. The care system of claim 19, wherein the posture module is programmed to validate the predetermined horizontal supine baseline gravity vector, the predetermined horizontal prone baseline gravity vector, the predetermined horizontal left lateral decubitus baseline gravity vector, and the predetermined horizontal right lateral decubitus baseline gravity vector when the reviewed cross products approximately equals the predetermined vertical baseline gravity vector.

22. The care system of claim 18, further comprising an external device operating an application programmed to:

prompt the patient to assume a vertical position and receive an indication that the patient is in the vertical position for establishing the predetermined vertical baseline gravity vector.

23. The care system of claim 18, further comprising an external device operating an application programmed to:

prompt the patient to assume a horizontal supine position and receive an indication that the patient is in the horizontal supine position for establishing the predetermined horizontal supine baseline gravity vector.

24. The care system of claim 23, wherein the posture module is programmed to determine the predetermined horizontal prone baseline gravity vector, the predetermined horizontal left lateral decubitus baseline gravity vector, and the predetermined horizontal right lateral decubitus baseline gravity vector from the established horizontal supine baseline gravity vector.

25. The care system of claim 23, wherein the application is further programmed to:

prompt the patient to assume a horizontal prone position and receive an indication that the patient is in the horizontal prone position for establishing the predetermined horizontal prone baseline gravity vector;

prompt the patient to assume a horizontal left lateral decubitus position and receive an indication that the patient is in the horizontal left lateral decubitus position for establishing the predetermined horizontal left lateral decubitus baseline gravity vector; and prompt the patient to assume a horizontal right lateral decubitus position and receive an indication that the patient is in the horizontal right lateral decubitus position for establishing the predetermined horizontal right lateral decubitus baseline gravity vector.

26. The care system of claim 1, wherein the posture module is programmed to review at least one of sensed respiratory information of the patient, sensed cardiac waveform polarity information of the patient, and sensed cardiac waveform phase change information of the patient to estimate an orientation of the first implantable sensor relative to earth to calibrate information signaled by the first implantable sensor.

27. The care system of claim 1, wherein the posture module is programmed to perform at least one of:

a calibration routine to calibrate information signaled by the first implantable sensor upon determining the patient has waken from a state of sleep and changed posture;

prompt the patient to assume different postures and receive an indication that the patient has assumed a particular posture to calibrate information signaled by the first implantable sensor.

28. The care system of claim 1, wherein the posture model is programmed to receive at least one predetermined position indication value from a clinician following implantation of the first implantable sensor to calibrate information signaled by the first implantable sensor.

29. The care system of claim 1, wherein the posture module is programmed to calibrate information signaled by the first implantable sensor based upon a predicted position of the patient and to reference an internal clock in deriving a predicted position of the patient.

30. The care system of claim 29, wherein the posture module is programmed to designate the predicted position of the patient during a time the patient is typically sleeping.

* * * * *